(12) United States Patent
Corrales Flores et al.

(10) Patent No.: US 12,036,065 B2
(45) Date of Patent: Jul. 16, 2024

(54) MODULAR WIRELESS SYSTEM FOR MULTI-POINT SYNCHRONOUS MEASUREMENT OF CARDIAC AND VASCULAR INDICATORS, THEIR FUNCTION AND THE DIFFERENCES OVER TIME

(71) Applicants: Rafael Guillermo Corrales Flores, San Jose (CR); Yamilah Bouzid Jimenez, San Jose (CR); Jeiner Alberto Alvarado Fonseca, San Rafael Alajuela (CR); Laura Loaiciga Salazar, San Jose (CR)

(72) Inventors: Rafael Guillermo Corrales Flores, San Jose (CR); Yamilah Bouzid Jimenez, San Jose (CR); Jeiner Alberto Alvarado Fonseca, San Rafael Alajuela (CR); Laura Loaiciga Salazar, San Jose (CR)

(73) Assignee: Orbicor Technologies Sociedad Anonima, San Jose (CR)

( * ) Notice: Subject to any disclaimer, the term of this patent is extended or adjusted under 35 U.S.C. 154(b) by 0 days.

(21) Appl. No.: 17/167,883

(22) Filed: Feb. 4, 2021

(65) Prior Publication Data

US 2022/0240889 A1 Aug. 4, 2022

(51) Int. Cl.
*A61B 8/06* (2006.01)
*A61B 8/00* (2006.01)
(Continued)

(52) U.S. Cl.
CPC ............... *A61B 8/06* (2013.01); *A61B 8/02* (2013.01); *A61B 8/4433* (2013.01);
(Continued)

(58) Field of Classification Search
CPC ........... A61B 8/42; A61B 8/06; A61B 8/4433; A61B 8/02–065
See application file for complete search history.

(56) References Cited

U.S. PATENT DOCUMENTS

2006/0100530 A1* 5/2006 Kliot .................... A61B 5/0205
600/483
2009/0219108 A1* 9/2009 Zhao ........................ A61B 8/13
333/32

(Continued)

*Primary Examiner* — Angela M Hoffa
*Assistant Examiner* — Younhee Choi
(74) *Attorney, Agent, or Firm* — Allen, Dyer, Doppelt & Gilchrist, P.A.

(57) ABSTRACT

A wireless system and method for measuring and analyzing blood in a user's body is provided. The system includes a processing, power, and communication component (PPC) having a hardware unit and first housing enclosing the hardware unit; a probe having a piezoelectric crystal and second housing enclosing the piezoelectric crystal; a dock having a sensor and third housing enclosing the sensor. The second housing is spaced apart from the first housing. The third housing is adapted to removably couple to the first housing. The piezoelectric crystal can transmit an ultrasound wave into the body, receive a return ultrasonic wave, convert the return wave into an electrical signal, and transmit the signal to the sensor. The sensor is configured to receive and then transmit the electronic signal to the hardware unit, which is configured to wirelessly transmit a data set based on the electronic signal to a computer device.

6 Claims, 19 Drawing Sheets

(51) Int. Cl.
*A61B 8/02* (2006.01)
*A61B 8/08* (2006.01)

(52) U.S. Cl.
CPC .......... *A61B 8/4455* (2013.01); *A61B 8/4494* (2013.01); *A61B 8/488* (2013.01)

(56) References Cited

U.S. PATENT DOCUMENTS

| | | | |
|---|---|---|---|
| 2015/0327839 A1* | 11/2015 | Kim | A61B 8/00 600/447 |
| 2016/0135786 A1* | 5/2016 | Mullen | A61B 8/4427 600/459 |
| 2017/0100092 A1* | 4/2017 | Kruse | G01S 15/8997 |
| 2018/0000405 A1* | 1/2018 | Penders | A61B 8/4416 |
| 2018/0028159 A1* | 2/2018 | Hageman | A61B 8/4483 |
| 2018/0303419 A1* | 10/2018 | Muñoz | A61B 8/4477 |
| 2019/0069842 A1* | 3/2019 | Rothberg | A61B 8/429 |
| 2019/0269327 A1* | 9/2019 | Singh | A61B 8/56 |
| 2019/0269914 A1* | 9/2019 | Moaddeb | A61B 8/4227 |
| 2020/0261059 A1* | 8/2020 | Xu | A61B 8/06 |
| 2021/0038192 A1* | 2/2021 | Odungattu Thodiyil | A61B 8/5207 |
| 2021/0085280 A1* | 3/2021 | Van Heesch | G16H 50/30 |

* cited by examiner

MODULAR WIRELESS SYSTEM FOR MULTI-POINT SYNCHRONOUS MEASUREMENT OF CARDIAC AND VASCULAR INDICATORS, THEIR FUNCTION AND THE DIFFERENCES OVER TIME

FIELD

The present disclosure relates to a wireless system and method for measuring cardiac and vascular function, and more particularly to a modular wireless system and method of accurately measuring and analyzing indicators of cardiac and vascular function, including aortic pulse wave, pulse transit time, aortic pulse wave velocity, blood flow velocity, blood turbulence, heart rate, or combinations thereof.

BACKGROUND

Non-communicable diseases account for two-thirds of all deaths in the world, and cardiovascular diseases make up almost half of those deaths. Most indicators of cardiac and vascular function, including heart rate, aortic pulse wave, pulse transit time, aortic pulse wave velocity, blood flow velocity, and blood turbulence can only be measured accurately at a clinic or hospital.

Doppler ultrasound is a non-invasive procedure used in medical imaging to examine blood flow through vasculature vessels, including the major arteries and veins in the body of a patient. Ultrasound waves transmitted into specific points of the body interact with the blood cells flowing in the vascular system. That interaction causes a change in pitch, such that the reflected sound waves are different than the transmitted sound waves (i.e., Doppler shift). The pitch changes can be processed and displayed in a graphical view, which can be used to evaluate blood flow and aortic wave form changes. Such changes are helpful to diagnose abnormalities that may increase the risk of stroke, heart failure, or other cardiovascular disorders. Such abnormalities include blocked or narrowed arteries, arterial plaque, blood clots in veins, reduced blood flow, etc.

Existing devices for measuring cardiac and vascular indicators of heart and peripheral arterial disease are either invasive or non-invasive. An implant is an example of an invasive device, which requires surgery to place the device within a patient's body. Surgery, and therefore invasive devices, carries an inherent risk of infection and is generally unfavorable. Non-invasive devices exist only for a clinical setting, as their use requires a medical professional. Existing non-invasive devices for home use lack the necessary technology for obtaining and configuring synchronous and clinically accurate data from multiple positions on the patient's body.

Telemedicine allows healthcare professionals to evaluate, diagnose, and treat patients at a distance using telecommunications technology. Without the necessary technology for non-invasive home-use devices, a highly accurate analysis of a patient's cardiovascular system is not possible. For the foregoing reasons, there is a need for non-invasive home-use devices that can be used in telemedicine for the analysis of different variables over time.

SUMMARY

In various embodiments, a wireless system for measuring and analyzing blood flow in a body of a user is provided. The system includes a processing, power, and communication component (PPC) having a hardware unit and first housing enclosing the hardware unit; a probe having a piezoelectric crystal and second housing enclosing the piezoelectric crystal; a dock having a sensor and third housing enclosing the sensor. The second housing is spaced apart from the first housing. The third housing is adapted to removably couple to the first housing. The piezoelectric crystal can transmit an ultrasound wave into the body, receive a return ultrasonic wave, convert the return wave into an electrical signal, and transmit the signal to the sensor. The sensor is configured to receive and then transmit the electronic signal to the hardware unit, which is configured to wirelessly transmit a data set based on the electronic signal to a computer device.

In some embodiments, the wireless system comprises a plurality of PPCs, docks, and probes; and each hardware unit in the plurality of PPCs is in wireless communication with all other hardware units in the plurality of PPCs and in wireless communication with a user device.

In some embodiments, the user device comprises an analytical software configured to interpret the data sets received and an embedded software to drive all hardware components and synchronize all hardware units and the data sets received from the plurality of PPCs; and to display information based on the synchronized data sets.

In some embodiments, the displayed information comprises cardiovascular indicators of heart function, including aortic pulse wave, pulse transit time, aortic pulse wave velocity, blood flow velocity, blood turbulence, and a combination thereof.

In some embodiments, a method for measuring and analyzing blood in a body of a user is provided. The method can include providing the wireless system for measuring and analyzing blood flow in a body of a user; transmitting acoustic energy from one or more piezoelectric crystals to an arterial target inside the user's body; receiving acoustic energy from the user's body in the one or more piezoelectric crystals, and transmitting the acoustic energy to a sensor in the dock of the wireless system; receiving and converting the acoustic energy into one or more electric signals; and transmitting the one or more electric signals to an app on the user's device for analyzing the measured values to obtain a parameter value indicative of a characteristic of the fluid.

In some embodiments, the wireless system utilized in the method comprises a plurality of PPC components, and the electric signals transmitted to the app on the user's device includes a plurality of information received from each PPC component in the plurality of PPC components. In some embodiments, the plurality of information received from each PPC component is analyzed simultaneously to provide an accurate parameter value.

Additional features and advantages of the embodiments disclosed herein will be set forth in the detailed description that follows, and in part will be clear to those skilled in the art from that description or recognized by practicing the embodiments described herein, including the detailed description which follows, the claims, as well as the appended drawings.

Both the foregoing general description and the following detailed description present embodiments intended to provide an overview or framework for understanding the nature and character of the embodiments disclosed herein. The accompanying drawings are included to provide further understanding and are incorporated into and constitute a part of this specification. The drawings illustrate various embodi-

BRIEF DESCRIPTION OF THE DRAWINGS

The features and advantages of the present disclosure will be more fully described in, or rendered obvious by the following detailed description of the preferred embodiments, which are to be considered together with the accompanying drawings wherein like numbers refer to like parts and further, wherein.

DETAILED DESCRIPTION

Figure 1:
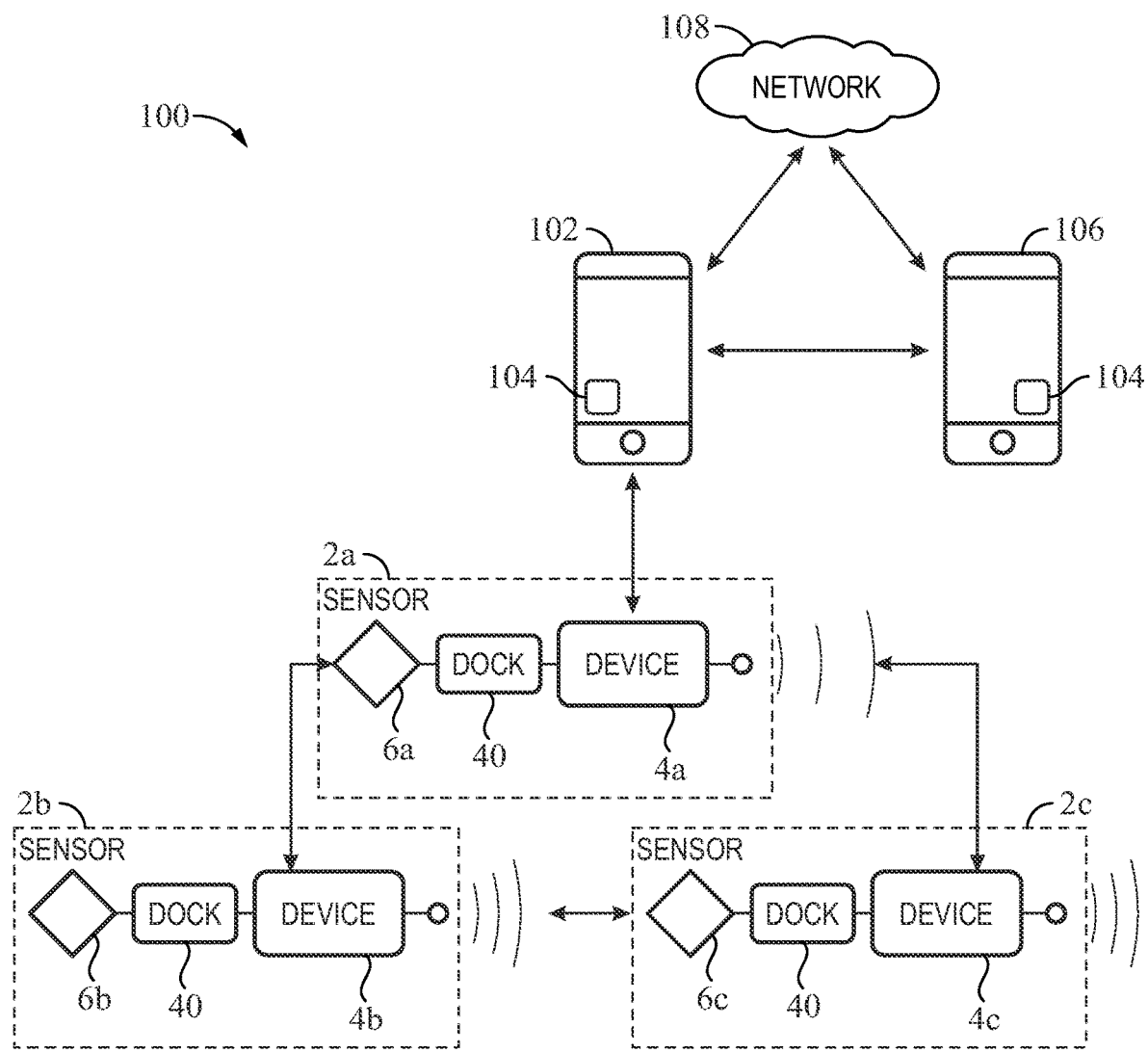
FIG. 1 is a block diagram of a wireless system, in accordance with some embodiments described herein.

Reference will now be made in detail to the present preferred embodiment(s), and examples of which is/are illustrated in the accompanying drawings. Whenever possible, the same reference numerals will be used throughout the drawings to refer to the same or like parts.

In various embodiments, as shown in FIGS. 1-21, a wireless system 100 for the simultaneous measurement and analysis of several critical cardiac, vascular, and external medical indicators in the body of a user is provided. The diagram in FIG. 1 provides an overview of an example wireless system 100. In some embodiments, the system 100 includes a combination device 2 or a plurality of combination devices (e.g., 2a, 2b, 2c, etc.). In such embodiments, each combination device 2 comprises a processing, power, and communication component or "PPC" 4 (e.g., 4a, 4b, 4c, etc.), an ultrasound sensor component or "probe" 6 (e.g 6a, 6b, 6c, etc.), and a docking component or "dock" 40. In FIG. 1, each combination device (e.g., 2a) is in communication with each of the other combination devices (e.g., 2b, 2c, etc.) and vice versa. Further, in some embodiments, the one or more combination devices 2 are in communication with a user device 102, which includes a cross-platform program or "app" 104. In such embodiments, as shown in FIG. 1, the user device 102 is in communication with one or more referring devices 106 having the same app 104, either directly or via a network 108.

In various embodiments, the user device 102 and the referring device 106 can be a computing device, such as a smartphone, tablet computer, smart glasses, smartwatch, or any other type of computing device. For example, user device 102 could be a handheld computing device (e.g., a smartphone, tablet computer, etc.).

In various embodiments, the cross-platform program or app 104 is downloadable and can be implemented on multiple devices, including, e.g., the user device 102 and the referring device 106. The app 104 can be configured to perform the desired functions required by the system 100.

In various embodiments, the network 108 can correspond to a local area network, wide area network, the Internet, a direct peer-to-peer network (e.g., device to device Bluetooth, etc.), and/or an indirect peer-to-peer network (e.g devices communicating through a server, router, or other network device). Network 108 can represent a single network or multiple networks. The communication network 108 used by the various devices of system 100 may be selected based on the proximity of the devices to one another or some other factor. For example, when user device 102 and referring device 106 are near each other (e.g., within a threshold distance, within direct communication range, etc.), user device 102 may exchange data using a direct peer-to-peer network. However, when user device 102 and referring device 106 are not near each other, user device 102 and referring device 106 may exchange data using a peer-to-peer network (e.g., the Internet).

Figure 2:
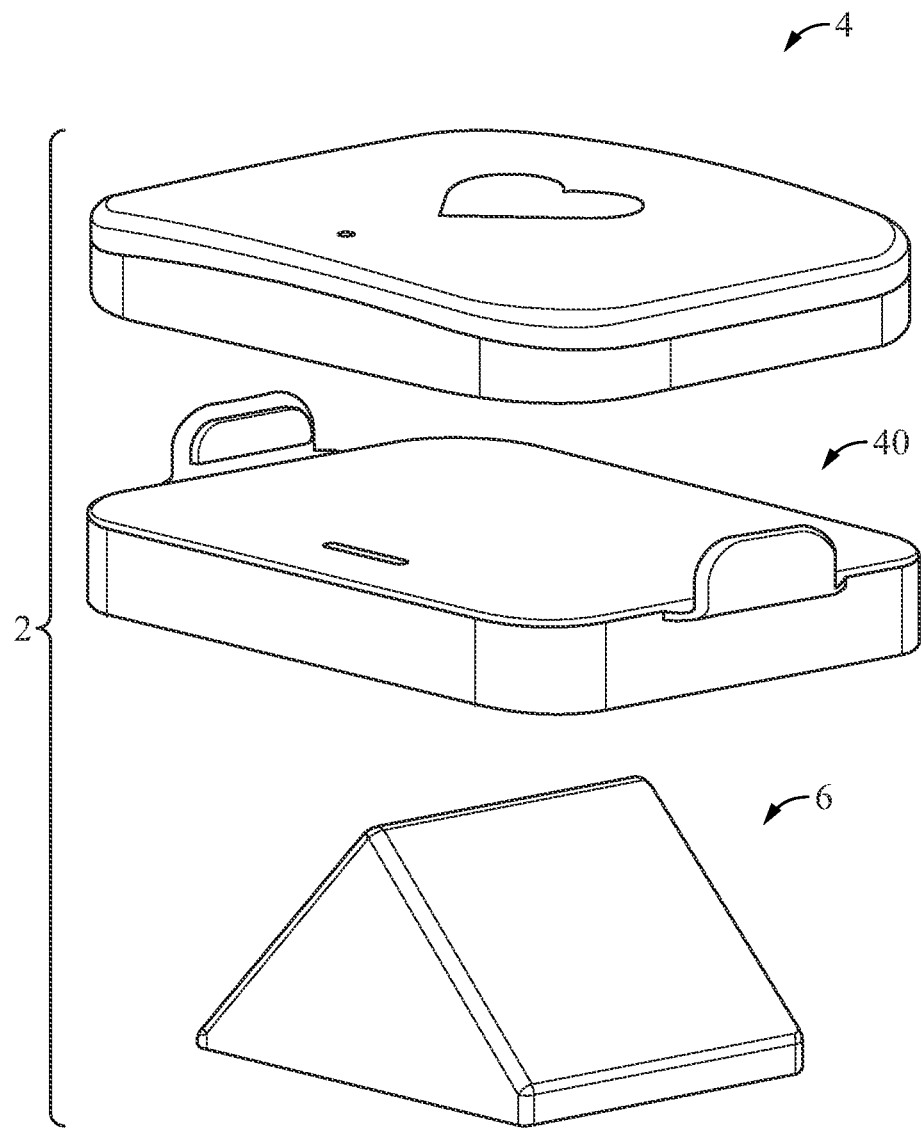
FIG. 2 is an oblique view of a combination device of the wireless system in FIG. 1, in accordance with some embodiments described herein.

FIG. 2 shows a combination device 2 comprising a PPC 4, a probe 6, and a dock 40. The size and shape of the PPC 4 is not particularly limited other than the practical restraints provided by its desired uses (e.g. where it is placed or attached on the user's body). In FIG. 2, for example, the PPC 4 has a generally rectangular prism shape with rounded corners. However, other shapes are contemplated, such as, e.g., a cylinder or elliptical cylinder.

Figure 3:
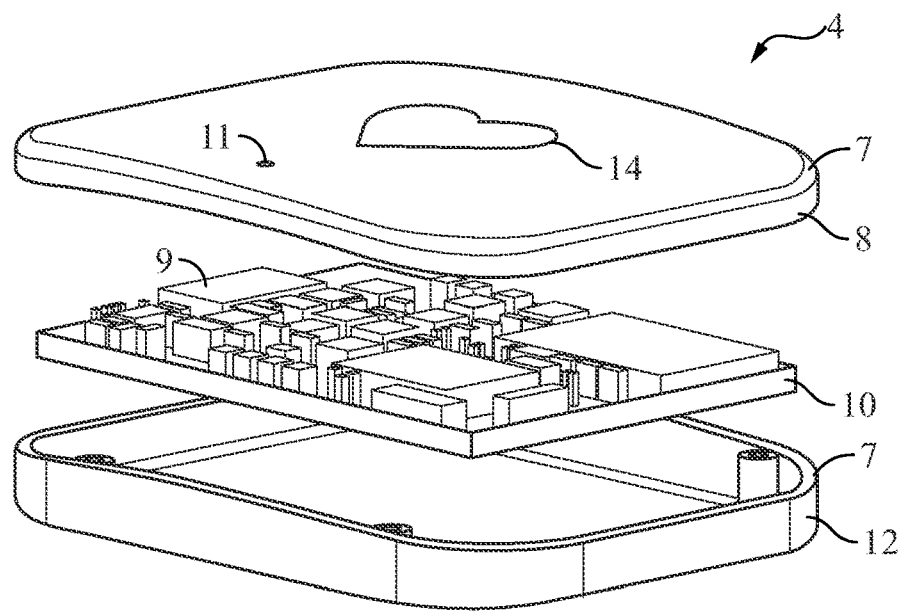
FIG. 3 is an exploded view of the PPC in FIG. 2, in accordance with some embodiments described herein.

FIG. 3 is an exploded view of the PPC 4. In some embodiments, the PPC 4 comprises a housing 7, which includes a top 8 and a bottom 12. In such embodiments, the top 8 and bottom 12 are coupled with one another to form the housing 7. In some embodiments, the top 8 and bottom 12 are removably coupled with one another. In some embodiments, the top 8 of PPC 4 comprises a button 14, which serves as an actuating device for, among other things, activating or deactivating the PPC 4. The size and shape of the button 14 is not particularly limited. For example, instead of being in the shape of a heart, the button 14 can be a circle, square, star, etc. In some embodiments, the PPC 4 comprises a light 11, including a LED, which in some embodiments can be multicolored, which indicates, among other things, the status, function, battery level, identity within the system 100. In some embodiments, the PPC 4 is activated when the light 11 is illuminated and deactivated when it is not illuminated. In some embodiments, the PPC 4 comprises a hardware unit 10. In such embodiments, the hardware unit 10 comprises a circuit with a plurality of components (e.g., printed circuit board). For example, the hardware unit 10 can include a light 9 (e.g., LED) for illuminating the indicator 11. The various components and functions of hardware unit 10 are discussed further in the context of FIGS. 9, 10, and 11.

Figure 4:
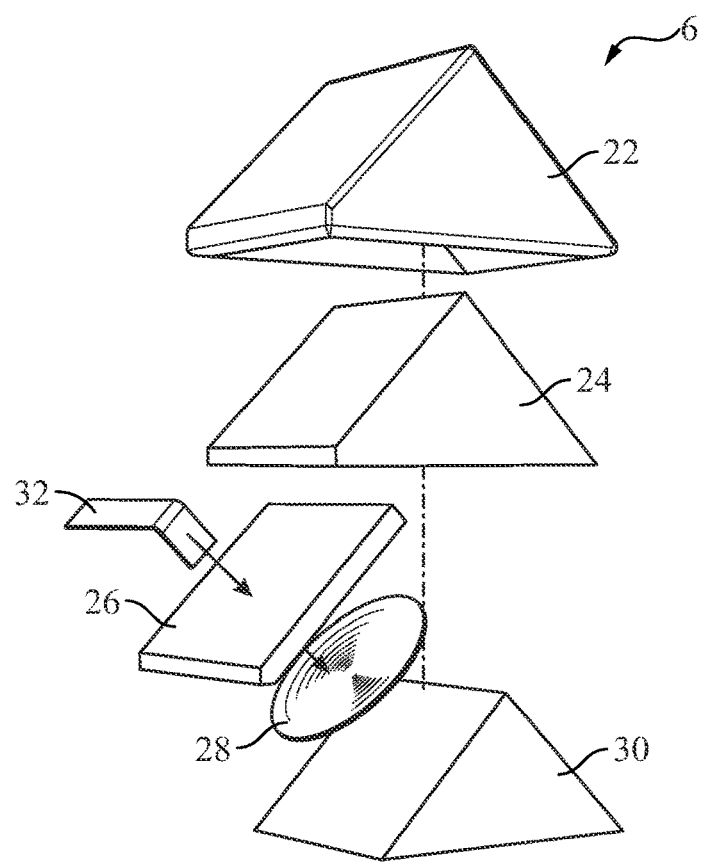
FIG. 4 is an exploded view of the ultrasonic piezoelectric crystal and housing of the ultrasound probe in FIG. 2, in accordance with some embodiments described herein.

FIG. 4 is an exploded view of the probe 6. In some embodiments, the probe 6 comprises a housing 22. The size and shape of housing 22 is not particularly limited. In some embodiments, the housing 22 has a generally triangular prism shape with an elevated rectangular base. Other shapes and configurations are contemplated. For example, the triangular prism shape can have a non-elevated rectangular base, or the shape can be cubic or a rectangular prism. In some embodiments, the probe 6 comprises a piezoelectric crystal 28. In some embodiments, the piezoelectric crystal 28 is positioned between a pair of acoustic matching layers (e.g., upper layer 26 and a corresponding lower layer 30). In such embodiments, the lower layer 30 has a substantially planar bottom surface, which maximizes contact with the user's skin. In some embodiments, the probe 6 comprises a cable 32 coupled to the piezoelectric crystal 28 through the upper acoustic matching layer 26. In some embodiments the probe 6 comprises an acoustic barrier 24, positioned between the cable 32 and upper acoustic matching layer 26 and the housing 22. In some embodiments, the cable 32 carries and/or transmits the electric current to and from the piezoelectric crystal 28 and the sensor 44 positioned inside of the dock 40 (see FIGS. 5 and 7).

In some embodiments, the piezoelectric crystal 28 is positioned at a 45-degree angle relative to the surface of the user's skin to measure the speed of the blood pulsing through the arteries by using the Doppler shift of the ultrasound waves emitted versus those received back. The 45-degree angle provides an accurate measurement of the Doppler shift because it is close to parallel with the direction of blood travel in the user's body. In such embodiments, the positioning of the piezoelectric crystal 28 therefore optimizes the functions of transmitting ultrasound waves into the body, receiving the returned wave, and converting the returned wave into an electrical signal (a voltage). In some embodiments, the probe 6 contains one or more sensors in addition to the piezoelectric crystal 28. For example, the probe 6 can include a dual element ultrasound transducer or a multi-element ultrasound array, comprising a plurality of piezoelectric crystals, thin films, and/or microelectromechanical systems (MEMS). In some embodiments, the probe 6 contains other sensors, such as microphones, thermal sensors, and/or sweat chemistry analytic sensors, which can be included in MEMS or thin film technologies.

In some embodiments, the piezoelectric crystal 28 is the active part of an ultrasound transducer, which can carry out the dual function of a transceiver. In such embodiments, the piezoelectric crystal 28 is capable of generating ultrasound energy by converting electrical signals into ultrasound (transmitter function) and sensing ultrasound energy and converting the same into electrical signals (receiver function). In some embodiments, the ultrasound transducer 6 contains a piezoelectric crystal 28 capable of measuring changes in force, pressure, acceleration, or strain and converting the changes into an electrical charge. In some embodiments, the piezoelectric sensor is a piezoelectric disk that is capable of generating a voltage when deformed in response to changes in force, pressure, temperature, acceleration, or strain.

In some embodiments, the ultrasound energy is in the form of a continuous wave or "CW" Doppler, in which ultrasound waves are continuously emitted from the piezoelectric crystal and the reflections of the waves are analyzed continuously. This process is possible because two or more different sets of piezoelectric crystals are utilized (one set for sending ultrasound and the other for analyzing reflected sound waves). In some embodiments, the probe 6 can use a single piezoelectric crystal 28 to emit and receive pulsed ultrasound signals (PW). In some embodiments, the probe 6 can use dual piezoelectric crystals to emit and receive continuous ultrasound signals (CW).

Figure 5:
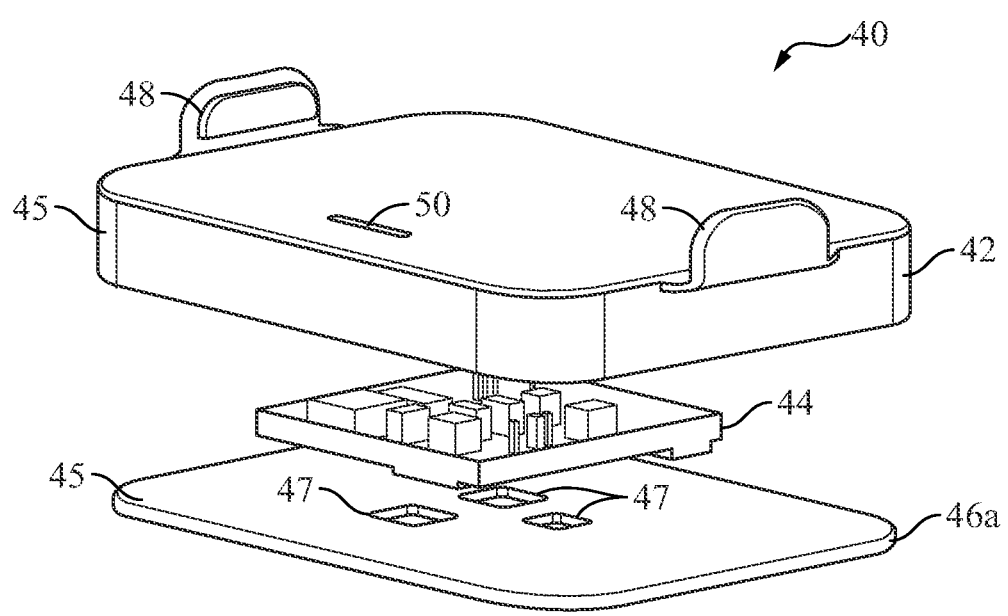
FIG. 5 is an exploded view of a dock of the wireless system in FIG. 1, in accordance with some embodiments described herein.

FIG. 5 is an exploded view of a docking component or "dock" 40. In some embodiments, the dock 40 comprises a sensor 44 and a housing 45 enclosing the sensor 44. In some embodiments, the housing 45 comprises a top 42 and bottom 46. In such embodiments, the top 42 and bottom 46 are coupled with one another to form the housing 45. In some embodiments, the top 42 and bottom 46 (e.g., 46a, 46b) are removably coupled to one another. In some embodiments, the top 42 comprises an upper surface configured to receive a PPC 4. In such embodiments, the top 42 comprises a pair of clips 48 that secure the PPC 4 to the dock 40. The clips 48 are attached to opposing sides of the dock 40. In some embodiments, for example, the clips 48 include a material (e.g., cushion or padded material) that secures the PPC 4 through compressive pressure and/or friction or magnetic coupling. Although two clips 48 are shown on the top 42 in the embodiment in FIG. 5, additional clips are contemplated. For example, the top 42 can include four clips, such that there is one clip on each side of the generally rectangular shaped top 42. In some embodiments, the dock 40 comprises a connector 50, which is adapted to receive a corresponding connector from the PPC 4. The connector 50, in some embodiments, is a multipin connector system that permits the transfer of electric current to sensor 44 and probe 6.

In some embodiments, the sensor 44 is a chipset comprising multiple sensor elements capable of communicating with the hardware unit 10 in the PPC 4. In some embodiments, the multiple sensor elements include a heart rate monitor, oximeter, and/or temperature sensor. In some embodiments, additional sensor elements are included (e.g., microphones, galvanic response, etc.). In such embodiments, the multiple sensor elements are capable of communicating with the MCU 110 through the sensor port 152 and comm port 150. The sensor 44 also communicates with the piezoelectric crystal 28 in probe 6, or both the piezoelectric crystal 28 in probe 6 and the hardware unit 10 in the PPC 4. In some embodiments, the housing bottom 46 includes one or more through-holes 47. In such embodiments, the through-holes 47 provide an opening for sensor elements on the sensor 44 to contact the skin of the user.

Figure 6:
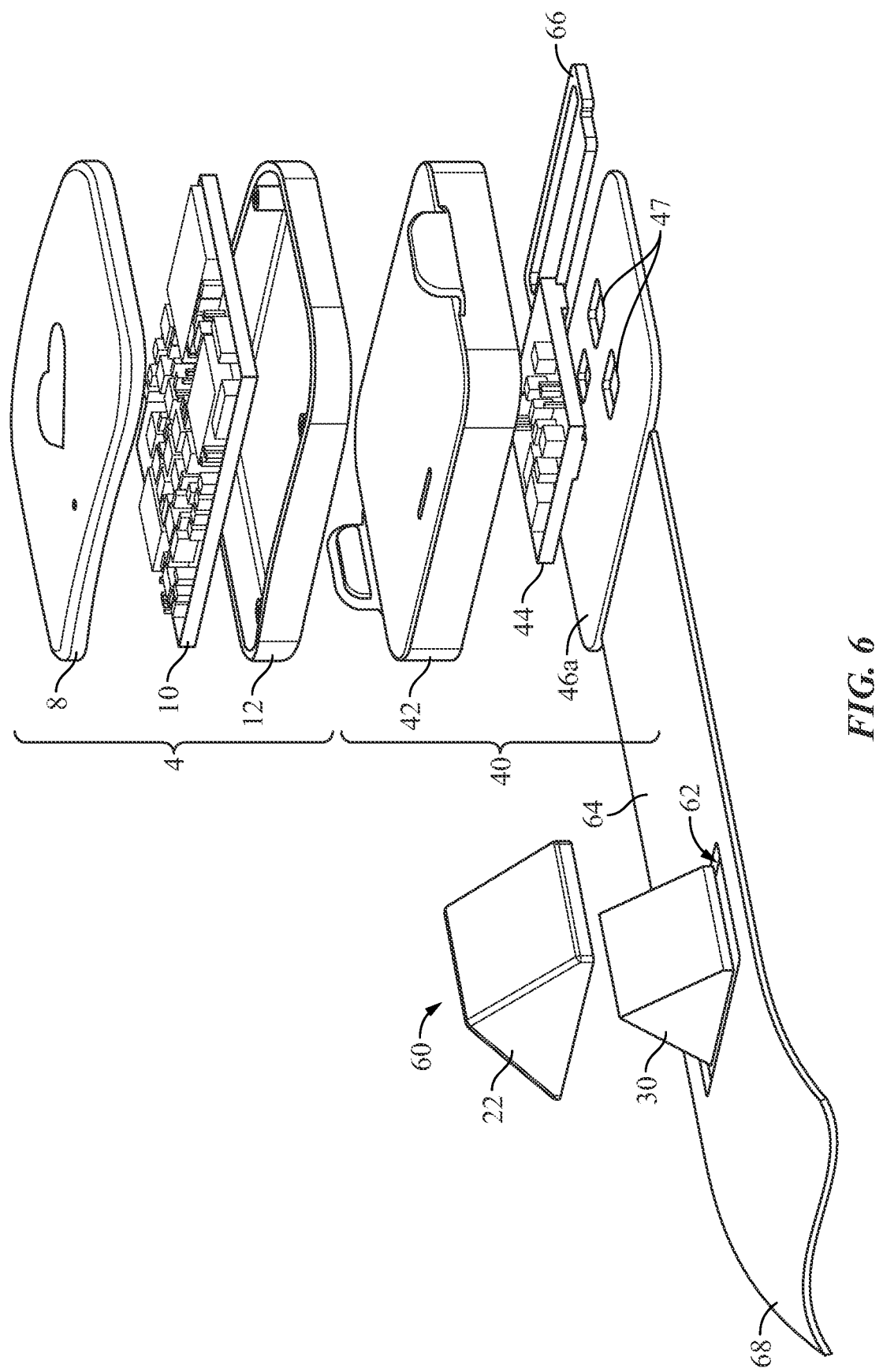
FIG. 6 is an exploded oblique view of the wireless system on a flexible band substrate, in accordance with some embodiments described herein.

In various embodiments, the probe 6, and dock 40 are attached to a substrate, while the PPC 4 is attached to the dock 40. For example, FIG. 6 shows an exploded view of the PPC, probe, and docking component assembled on a wearable substrate 64. The wearable substrate 64 is configured to wrap around various parts of the user's body, including, for example, the user's wrist, upper arm, neck, lower leg, upper leg, etc. In some embodiments, the wearable substrate 64 comprises first end 66 and a second end 68 opposite the first end 66. In some embodiments, the first end 66 is a clip configured to receive or couple to the second end 68. In some embodiments, the clip comprises an opening through which the second end 68 can be inserted through. In such embodiments, the wearable substrate 64 is configured so the second end 68 can be folded back onto itself and be removably attached thereto using, for example, a hook and loop fastener (e.g., Velcro).

In some embodiments, the dock 40 is coupled to the wearable substrate 64. In some embodiments, the dock 40 is permanently attached to the wearable substrate 64. In such embodiments, the bottom 46a of dock 40 is integrated into the wearable substrate 64 during manufacturing. In some embodiments, the dock 40 is integrated into the wearable substrate 64 at a position proximate to the first end 66. In such embodiments, the probe is attached to the wearable substrate at a position proximate to the second end 68, as shown in FIG. 6. In other embodiments, the dock 40 is removably coupled to the wearable substrate 64.

As shown in FIG. 6, the dock 40 and probe 6 are located on the wearable substrate 64 at a spaced distance from one another. The spaced distance is provided to allow the probe 6 to be in close proximity to the necessary artery and maximize ultrasound signal transmissions and reception. It is separated from the dock 40 to allow the probe 6 to adapt to the natural curvature of the human body. In some embodiments, the distance between the dock 40 and the probe 6 ranges from about 2 cm to about 15 cm, or about 3 cm to about 9 cm, or about 3.5 cm to about 7 cm. The ranges include the endpoints, any intermediate values, and subranges.

Figure 7:
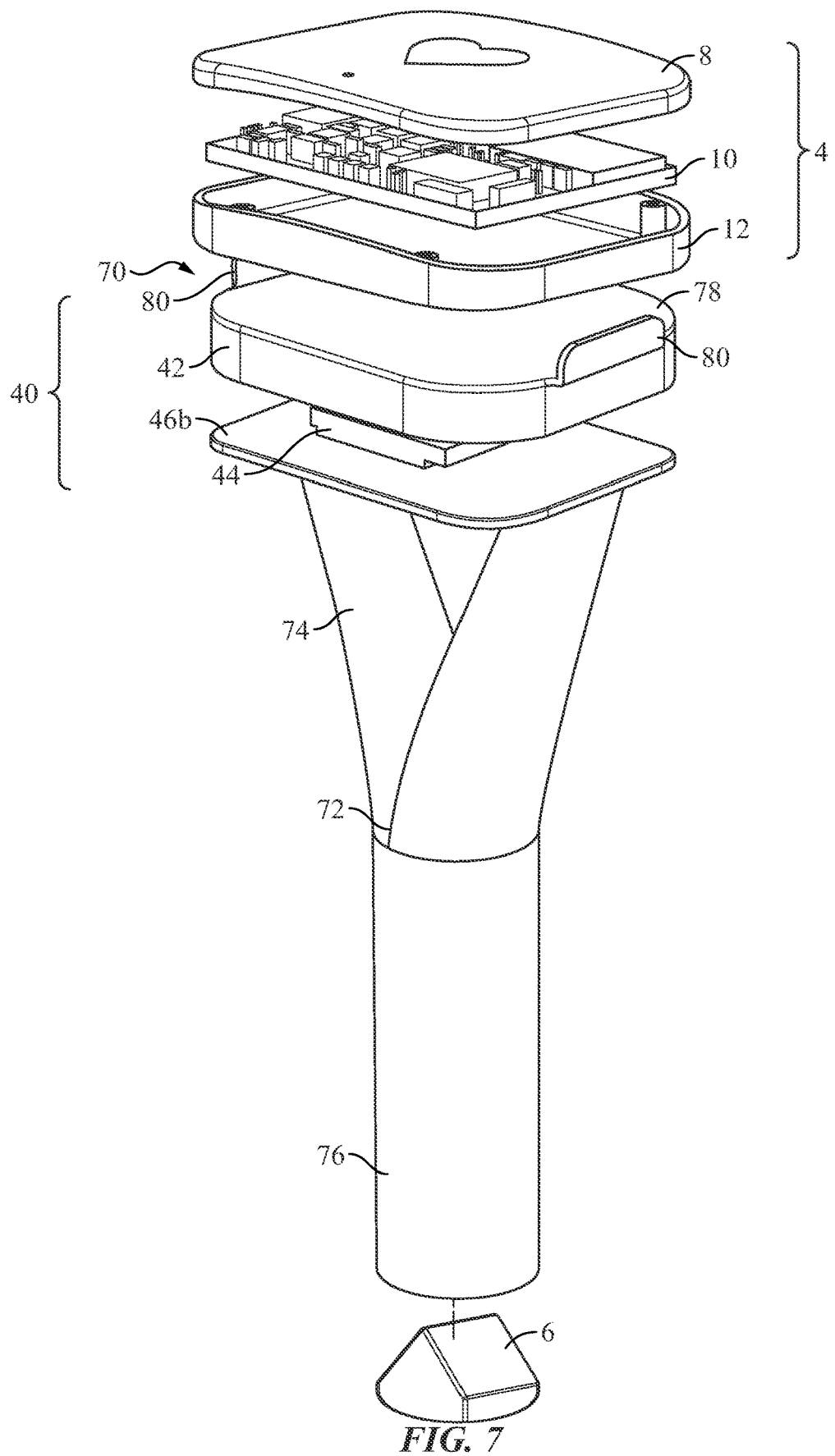
FIG. 7 is an exploded oblique view of the wireless system on a handheld vascular ultrasound pen/probe, in accordance with some embodiments described herein.

In various embodiments, alternative substrates are provided. For example, FIG. 7 shows a handheld device or "vascular pen" 70. In some embodiments, the pen 70 comprises a first end 74 and a second end 76 opposite the first end 74. In some embodiments, the first end 74 is coupled to a planar surface 46b, which also serves as the bottom of the dock 40. In some embodiments, the first end 74 is coupled to an intermediary component that is coupled to the planar surface 46b.

As shown in FIG. 7, in some embodiments, the dock 40 comprises a planar surface 78 having a pair of clips 80 located on opposing edges of the surface. In some embodiments, the clips 80 include a material (e.g., cushion, magnets or padded material) that secures the PPC 4 through compressive pressure, magnetic coupling and/or friction. Although two clips 80 are shown on the planar surface 78 in the embodiment in FIG. 7, additional clips are contemplated. For example, the planar surface 78 can include four clips, such that there is one clip on each side of the generally rectangular shape of planar surface 78.

In some embodiments, the pen 70 comprises a dock 40 having a connector 50 (see FIGS. 5 and 6), which is adapted to contact a corresponding connector from the PPC 4. In some embodiments, the connector 50 is a multipin connector system that permits the transfer of electric current between the sensor 44 and the probe 6.

In some embodiments, the vascular pen 70 comprises a probe 6 coupled to the second end 76. The probe 6 can be permanently or removably coupled to the second end 76. In various embodiments, the pen 70 is adapted to be held in a user's hand and contacted to the user's body in such a manner that the probe 6 can provide the desired blood velocity measuring functionality. Similar to the embodiment in FIG. 6, the vascular pen embodiment 70 positions the probe 6 and the PPC 4 a spaced distance from one another. The distance between the PPC 4 and the probe 6 is determined by the ergonomic needs created for the comfortable interaction with the hand of the user. In some embodiments, the probe 6 for the vascular pen 70 is the same size and shape as the probe 6 in the wearable device shown in FIG. 6. In some embodiments, the probe 6 for the vascular pen 70 has a different size or shape than that for the wearable probe in FIG. 6. Various sizes and shapes are contemplated, and the housing for the probe 6 will depend on how the probe 6 is integrated in the vascular pen 70.

Figure 8:
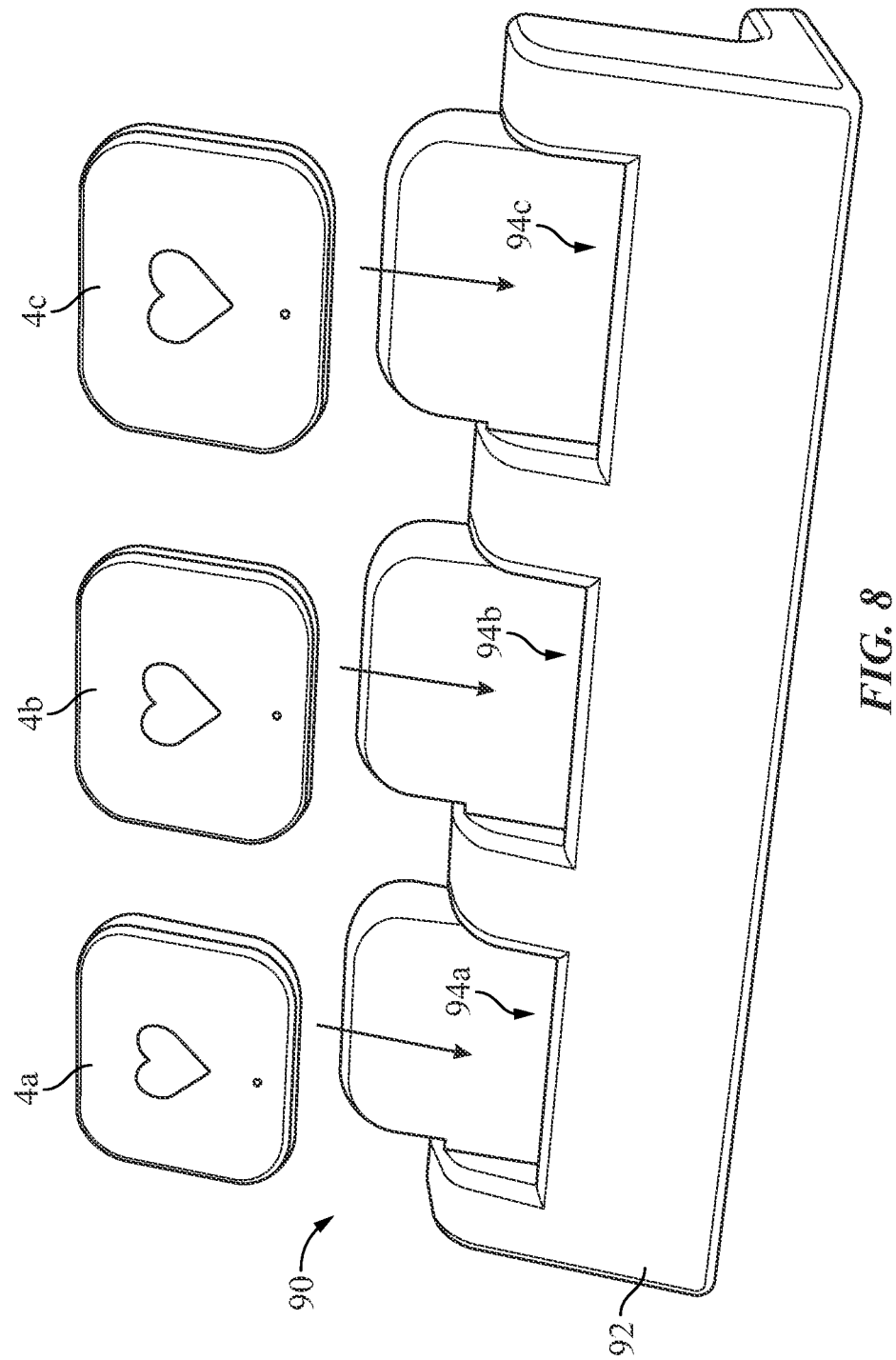
FIG. 8 is an oblique view of a wireless charger for a plurality of the PPC in FIG. 2, in accordance with some embodiments described herein.

In some embodiments, as shown in FIG. 8, the system includes a charging station or "charger" 90. The size and shape of the charger 90 is not particularly limited, and various sizes and shapes are contemplated. For example, the charger 90 can be configured to receive a single PPC 4 or a plurality of PPCs and vascular pen 70 holder. Accordingly, in some embodiments, the charger 90 has a single port 94 adapted to receive a single PPC 4. Alternatively, in some embodiments, the charger 90 includes a plurality of ports (e.g., 94a, 94b, . . . 94n), each adapted to receive a plurality of PPCs (e.g., 4a, 4b, . . . 4n), where n corresponds to the number of ports and PPCs. As shown in FIG. 8, the charger 90 has a body 92. In some embodiments, the PPC 4 is wirelessly charged. In some embodiments, the body 92 comprises a power source connector for receiving a power supply. In some embodiments, the power source connector is a receptacle for receiving a battery or plurality of batteries. In some embodiments, the power source connector is a configured to receive an energy source, including for example, an AC/DC adapter and/or an AC power supply input. In some embodiments, the body 92 comprises a plurality of power source connectors, including, e.g., at least one receptacle for receiving a battery or batteries and at least one connector for receiving a power supply input.

In some embodiments, the charger 90 further comprises a printed circuit board or "PCB" (not shown). The power received from power supply connector is transferred to the PCB, which may include various electrical components and circuits for controlling the charging of the PPC 4 battery. In some embodiments, for example, the PCB may include voltage regulators, current regulators, microprocessors and transistors to form a charging circuit responsible for starting, ramping, tapering, and ending charging voltage and current. Additionally, the charging circuit may monitor battery parameters such as voltage, capacity, and temperature. The PCB electrical circuit is coupled to a power source connector and electrical interface by wire or other form of electrical connector. In some embodiments, the charger 90 comprises an AC/DC power converter that converts the external AC power supply to a standard DC voltage that is usable by the charger 90 for charging the PPC(s) 4. In some embodiments, the charger 90 includes external indicators for identifying the charging status of the PPC(s) 4. In some embodiments, the charger 90 may be configured to charge the PPC wirelessly.

Figure 9:
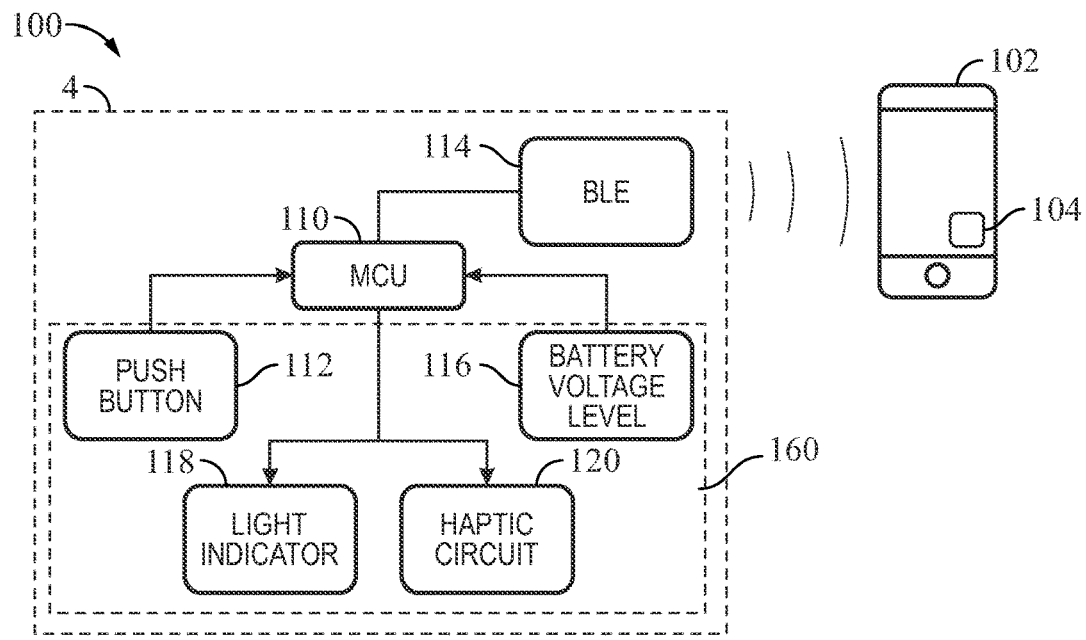
FIG. 9 is a block diagram of the User Interface Elements contained within the PPC in FIG. 2, in accordance with some embodiments described herein.

FIG. 9 is a block diagram showing the user interface elements of the PPC 4 in system 100, and also shows an interaction with user device 102. In some embodiments, the PPC 4 comprises one or more microcontroller unit(s) or "MCU" 110. As shown, the MCU 110 is in communication with a push button 112, which is configured to function as an actuator for powering the PPC 4 on or off, as well as for changing settings, function mode, or to reset the PPC 4 as needed. In some embodiments, the PPC 4 comprises a battery voltage level 116, which indicates the charge level of the battery. For example, in some embodiments, the PPC 4 comprises a rechargeable battery 142 and the battery voltage level 116 indicates the current capacity of the battery. In some embodiments, the PPC 4 comprises a Bluetooth low energy module or "BLE" 114. In such embodiments, the BLE 114 is configured to communicate wirelessly with any other PPCs 4 being used simultaneously, as well as the user device 102 when the app 104 is in communication with the PPC 4. In some embodiments, the PPC 4 comprises one or more user interface elements. For example, FIG. 9 shows a light indicator 118 and a haptic circuit 120. In some embodiments, the light indicator 118 provides notice of different data points, such as battery status, identification within the PPC 4 network, successful data gathering, among other things. In some embodiments, the haptic circuit 120 is a feedback module that vibrates to indicate to the user that a data threshold had been crossed, such as the on/off status, heart rate acquisition, beginning and completion sampling, etc. Other user interface elements, such as speaker or screen, are contemplated.

Figure 10:
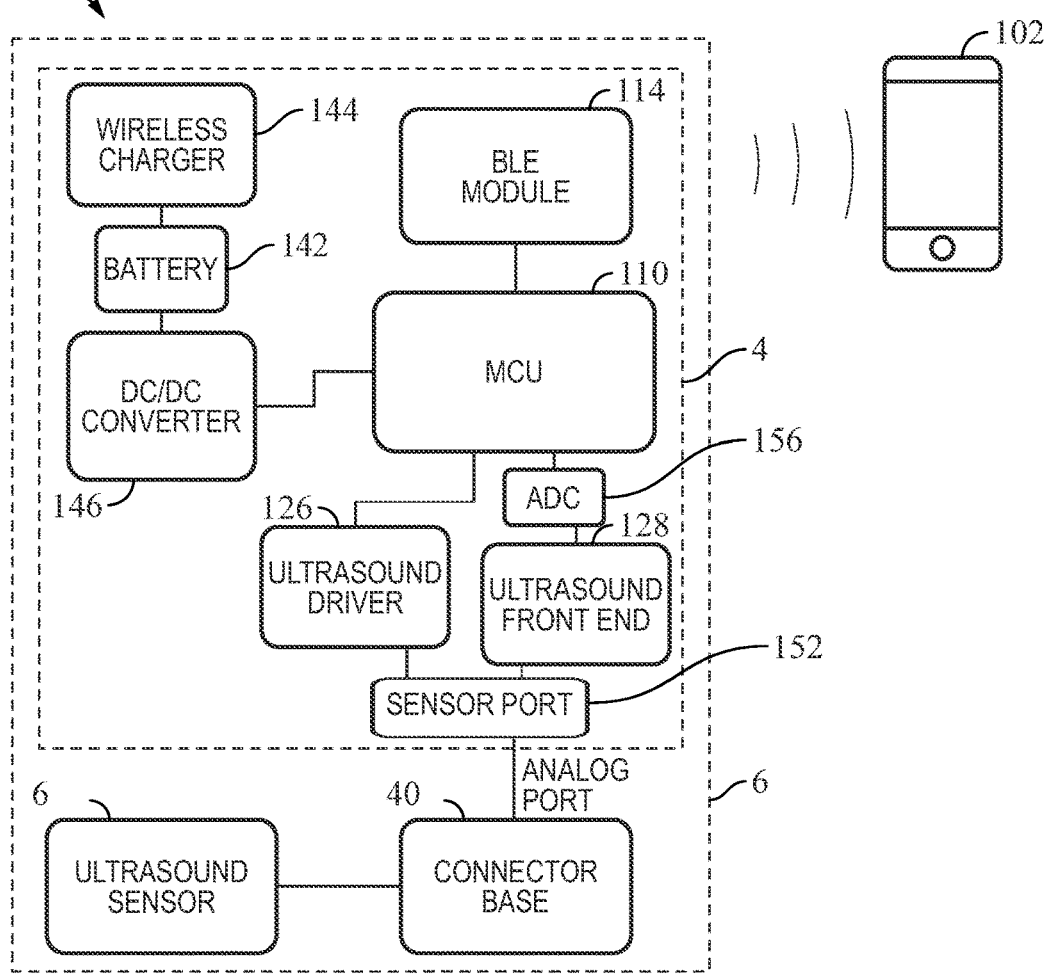
FIG. 10 is a block diagram of the wireless system of the handheld vascular ultrasound pen in FIG. 7 and the PPC in FIG. 2, in accordance with some embodiments described herein.
Figure 11:
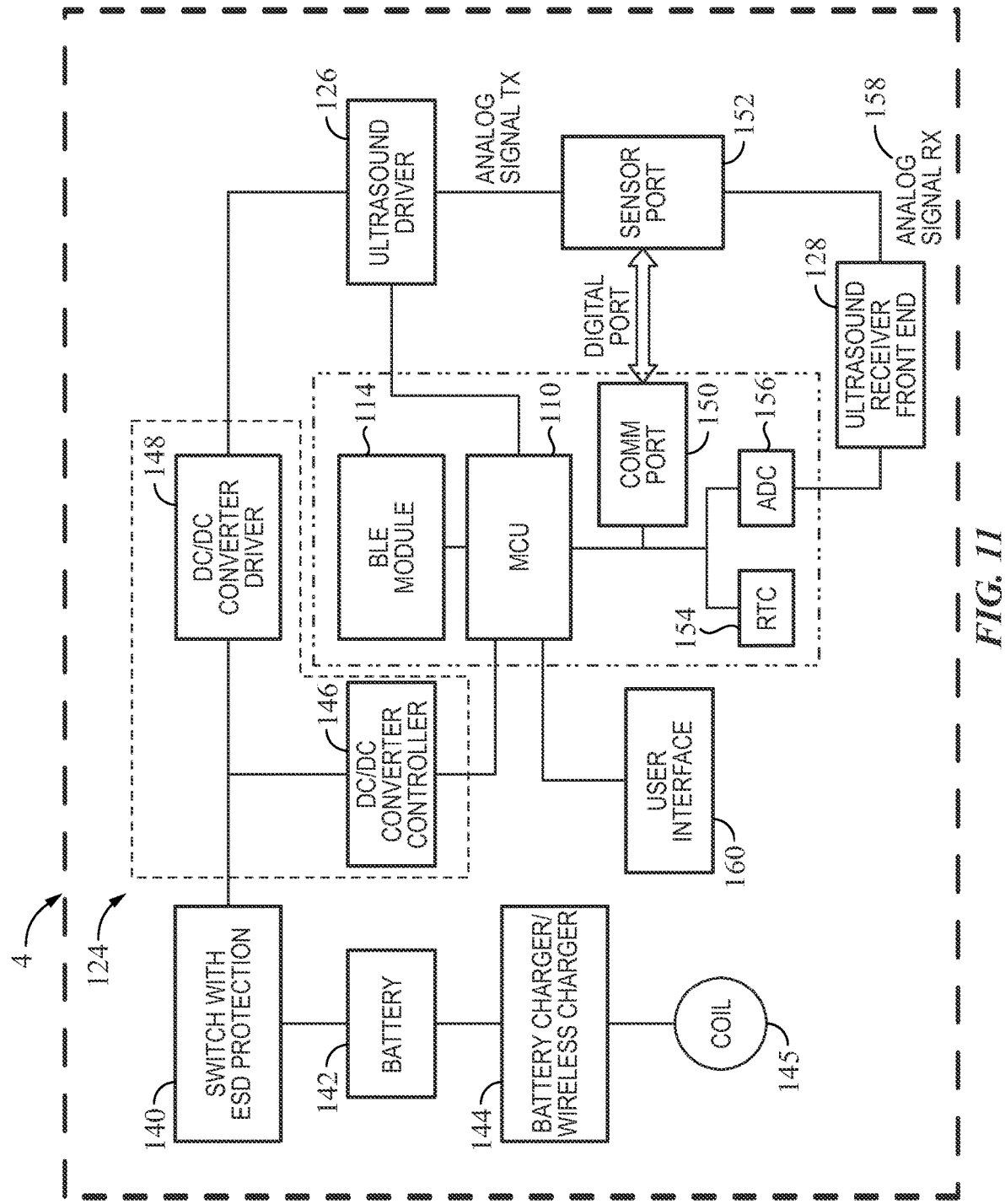
FIG. 11 is a block diagram of the PPC in FIG. 2, in accordance with some embodiments described herein.

FIG. 10 is a block diagram for the vascular pen 70, and also shows an interaction with user device 102. In some embodiments, pen 70 comprises a sensor array with a modified docking station to receive the PPC 4. In such embodiments, the PPC 4 is configured to communicate wirelessly with the user device 102 utilizing BLE 114. In some embodiments, the pen 70 further comprises an ultrasound driver 126 and an ultrasound front end 128 included within the PPC 4. The connector base 40 and the ultrasound transducer 6 are controlled and driven by the ultrasound driver 126 and the ultrasound front end 128, included within the PPC 4. In such embodiments, the ultrasound driver 126 and ultrasound front end 128 communicate with the ultrasound sensor 6 through the port 152. In some embodiments, the communication is analog, as shown in FIG. 11, digital, or a combination thereof. In some embodiments, the pen 70 measures and analyzes blood velocity in the user. In such embodiments, driver 126 provides an electric current to the ultrasound sensor 6, which converts electrical signals into ultrasound waves. In such embodiments, the ultrasound sensor 6 detects ultrasound energy waves returning from the user's body converting them into an electric current, which is filtered and amplified by the ultrasound front end 128.

FIG. 11 is a block diagram of the PPC 4. Similar to FIGS. 9 and 10, the PPC 4 in FIG. 11 comprises MCU 110 and BLE 114. In some embodiments, the PPC 4 further comprises a communication port 150 for digitally communicating with sensor port 152. In such embodiments, the sensor port 152 is connected to both the ultrasound driver 126 and the ultrasound receiver front end 128 through an analog signal (TX/RX) 158. In some embodiments, the MCU 110 is also connected to the user interface 160, and a DC/DC converter controller 146. The DC/DC converter driver 148 is in communication with the ultrasound driver 126 and a switch with electrostatic discharge or "ESD" protection 140. In some embodiments the DC/DC converter controller 146 is connected to the switch with ESD protection 140. In some embodiments the switch with ESD Protection 140 is connected to the battery 142. In some embodiments, the battery 142 is connected to the battery charger/wireless charger 144. In some embodiments, the MCU 110 is in communication with a real time clock or "RTC" 154 and an analog-to-digital converter or "ADC" 156. The ADC 156 is in further communication with the ultrasound receiver front end 128. In some embodiments, the RTC 154 functions as a master timekeeper for the synchronization of the multiple PPCs 4 and their corresponding sensor data, which is part of the system and critical for comparative analytics. In some embodiments, the system in FIG. 11 operates according to the following processes. The battery charger/wireless charger 144 transmits electricity to the battery 142 when the PPC 4 is in the charging station 90. The battery 142 transmits electricity to the MCU 110 and the ultrasound driver 126, passing through the switch with ESD protection 140 and the DC/DC converter controller 146 for the MCU 110 and through the DC/DC converter driver 148 for the ultrasound driver 126. In such embodiments, the user will power up the system and input the proper settings using the user interface 160. Once powered, the MCU 110 loads the embedded software and activates the Bluetooth low energy (BLE) module 114. The BLE module 114 establishes a communication channel between the system 100 and the user device 102. In such embodiments, the user utilizes the app 104 to transmit an instruction set to the MCU 110, utilizing a channel provide by the BLE module 114. In some embodiments, the MCU 110 activates the ultrasound driver 126 and sends electricity through the sensor port 152 to the ultrasound probe 6 as needed. The ultrasound probe 6 will return data in the form of an electric current modulated by the Doppler effect of the blood on the ultrasound waves. In such embodiments, this data arrives through the sensor port 152 in the form of an analog signal TX/RX 158 and is then transmitted to the ultrasound receiver front end 128. The ultrasound receiver front end 128 filters and amplifies the received analog signal 158, for transmittal to the analog-to-digital converter (ADC) 156. The ADC 156 converts the filtered and amplified analog signal to digital data for interpretation by the MCU 110. The MCU 110 transmits the obtained data to the user device 102 for interpretation, comparison, and analysis within the app 104. In some embodiments, for sensor types other than the ultrasound probe 6, the MCU 110 provides power, instructions, and receives digital data through the comm port 150 and the sensor port 152.

Figure 12:
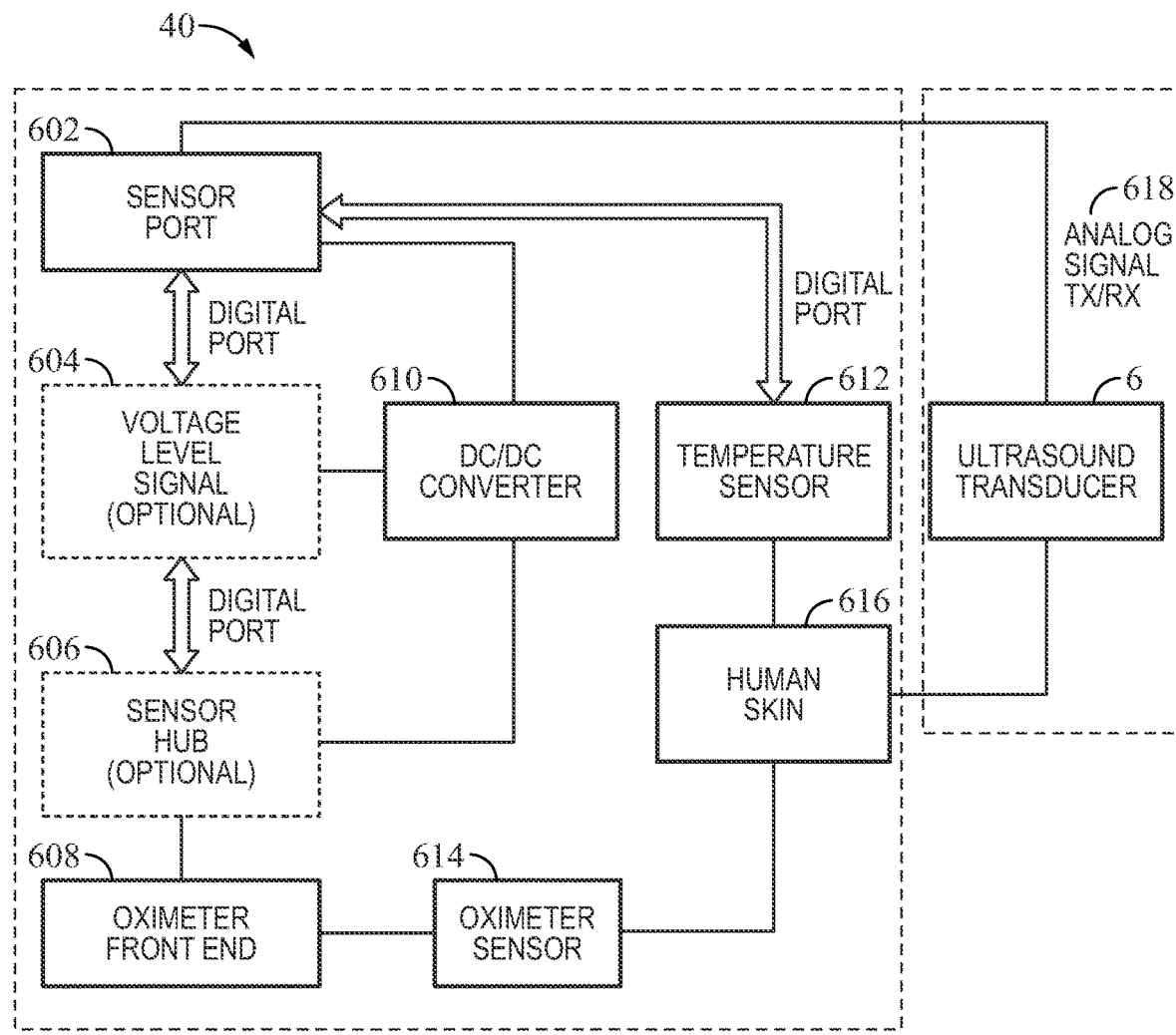
FIG. 12 is a block diagram of the ultrasound probe and dock base sensor array in FIG. 2 including the dock temperature sensor and oximeter sensor, in accordance with some embodiments described herein.

FIG. 12 is a block diagram of the dock 40. In some embodiments, the dock 40 is connected to the probe 6, the probe comprising an ultrasound piezoelectric crystal 28 that is connected to sensor port 602 via analog signal 618 (TX/RX). In some embodiments, the sensor port 602 is connected to the temperature sensor 612 via a digital port and DC/DC converter 610. In some embodiments, the sensor port 602 is further connected to the oximeter front end 608. The sensor port 602 connection to the oximeter front end 608 optionally includes intermediate connections through a digital port to a voltage level signal 604 and the sensor hub 606. In some embodiments, the oximeter front end 608 is connected to oximeter sensor 614, which is in contact with the user's skin 616. In some embodiments, the skin 616 is also in contact with the temperature sensor 612 and the ultrasound transducer probe 6.

FIG. 12 shows the sensor elements in the dock 40 and the ultrasound probe 6. In some embodiments, the sensors on the dock 40 receive power and instructions from the PPC 4 through the sensor port 602. The sensor port 602 sends instructions and power to the temperature sensor 612. The temperature sensor 612 reads the temperature on the user's skin 616 and returns digital data to the MCU 110, via the sensor port 602. The sensor port 602 transmits energy to the oximeter front end 608, through a DC/DC converter 610, which provides the appropriate voltage. In some embodiments, the oximeter front end 608 provides energy and controls the oximeter sensor 614. The oximeter sensor 614 interacts with the human skin 616, gathering oximetry and heart rate data, and then converts the data to digital data, which is then transmitted to the MCU 110 via the oximeter front end 608 and the sensor port 602.

Figure 13:
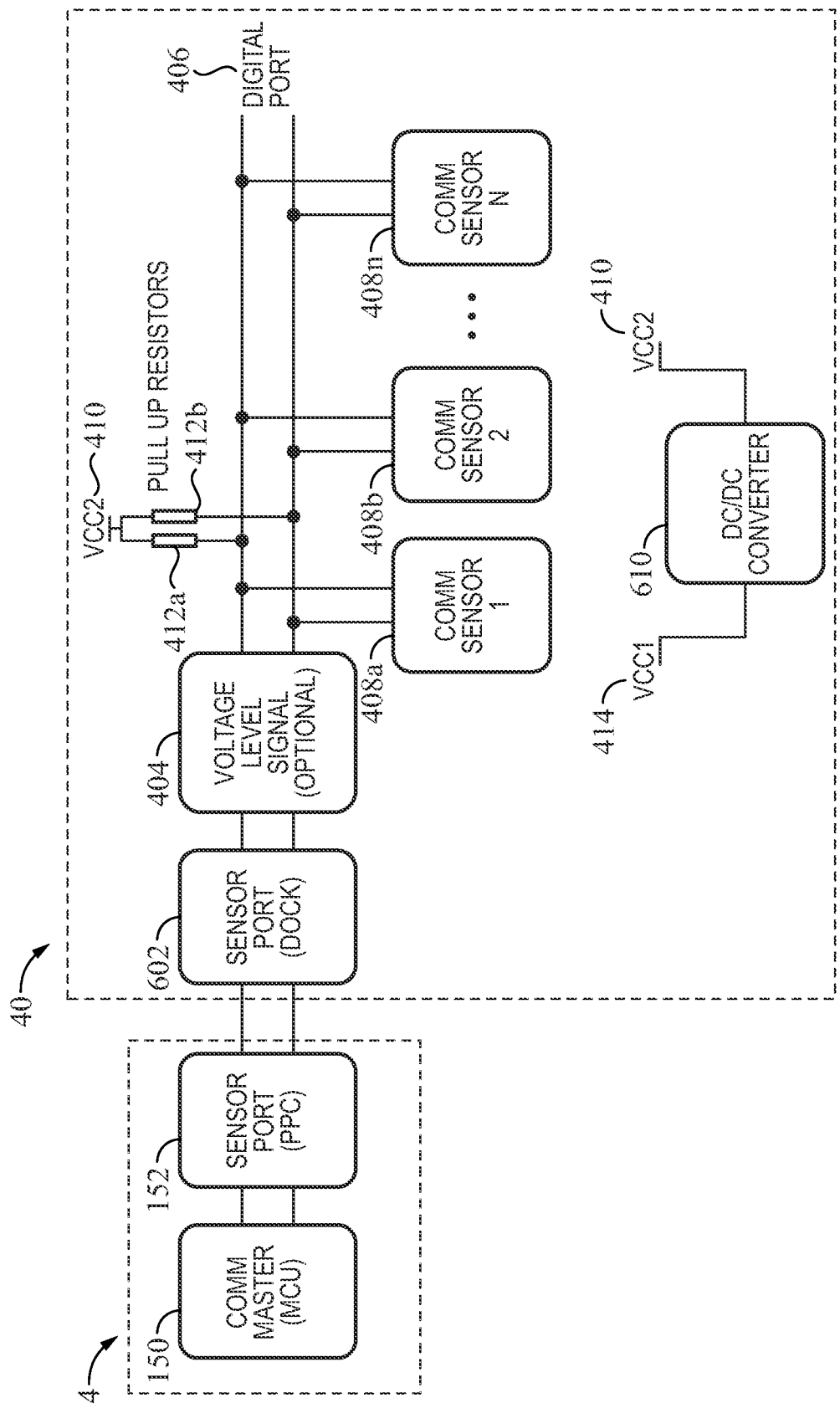
FIG. 13 is a block diagram of the communications design of the base/dock in FIG. 5, in accordance with some embodiments described herein.

FIG. 13 is a block diagram of the sensor port 152 and "COM-PORT" 150 in FIG. 11. In some embodiments, sensor port 152 comprises a digital port 406, and one or more sensors 408a, 408b ... 408n. In some embodiments, the sensor port 152 optionally comprises a voltage level signal 604. In some embodiments, the sensor port 152 comprises a pair of resistors 412a, 412b that are coupled on opposing sides of a second voltage common collector or "VCC2" 410. In such embodiments, VCC2 410 is connected to one end of the DC/DC convertor 416, which is connected on the opposing end to a first voltage common collector or "VCC1" 414.

Figure 14:
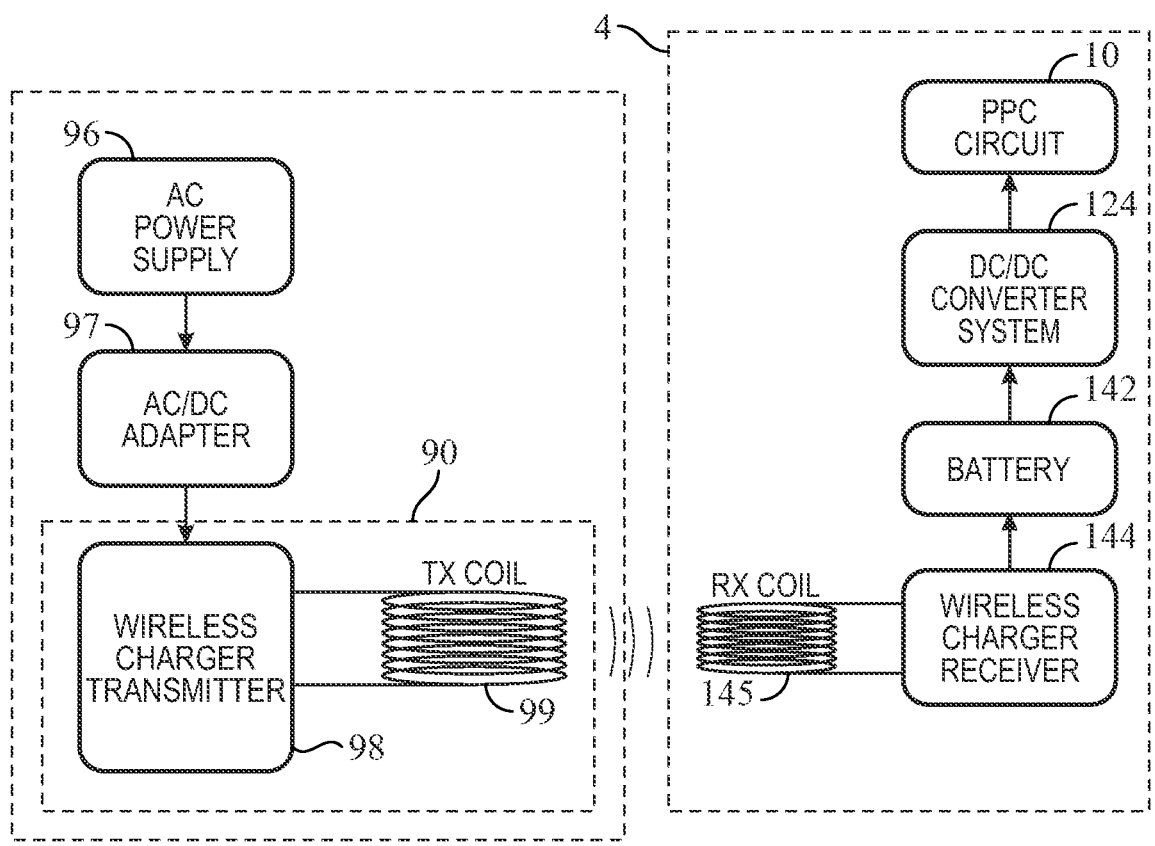
FIG. 14 is a block diagram of the charger in FIG. 8 and the receiving system in the PPC in FIG. 3, in accordance with some embodiments described herein.

FIG. 14 is a block diagram showing the components of the charger 90 and the relevant components of PPC 4. The charger 90 is shown on the left, and the PPC 4 is shown on the right. In some embodiments, the charger 90 comprises a wireless charging transmitter 98 and a TX coil 99. In such embodiments, the charger 90 is configured to receive DC energy from AC power supply 96 via AD/DC adapter 97. In some embodiments, the PPC 4 comprises a RX coil 145 configured to receive DC energy from the TX coil 99, which is relayed to a wireless charging receiver 144, which delivers the energy to a rechargeable battery 142. In some embodiments, the battery 142 sends the DC energy to a DC/DC converter system 124, which delivers the DC energy to the hardware unit 10 in PPC 4.

Example Processes

To enable the reader to obtain a clear understanding of the technological concepts described herein, the following processes describe specific steps performed in a specific order. However, one or more of the steps of a particular process may be rearranged and/or omitted while remaining within the contemplated scope of the technology disclosed herein. One or more processes and/or steps thereof, may be combined, recombined, rearranged, omitted, or executed in parallel to create different process flows that are within the contemplated scope of the technology disclosed herein. While the processes below may omit or briefly summarize some of the details of the technologies disclosed herein for clarity, the details described in the paragraphs above may be combined with the process steps described below to get a more complete and comprehensive understanding of these processes and the technologies disclosed herein.

Figure 15:
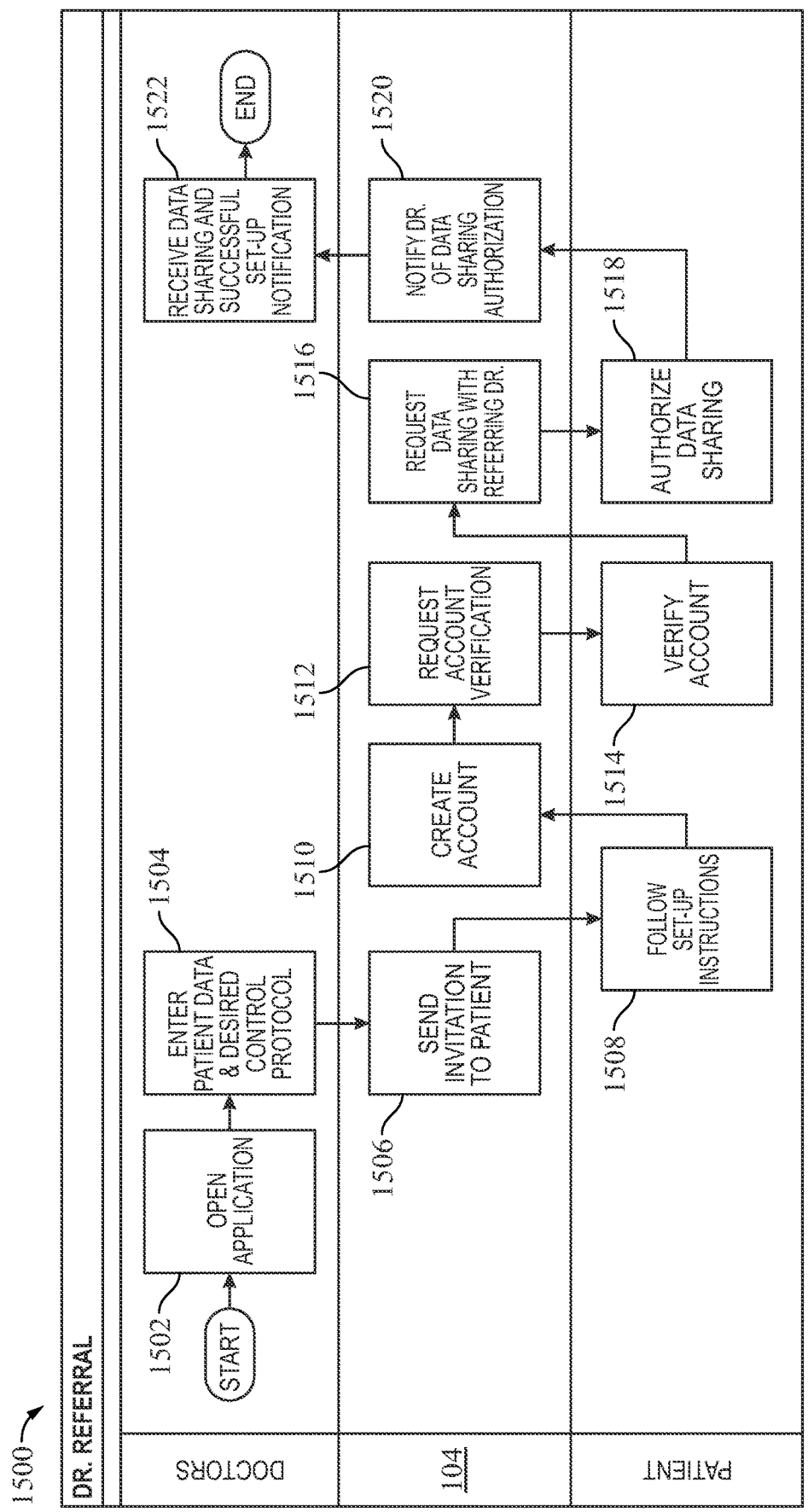
FIG. 15 is a flow diagram illustrating a process of a medical practitioner interacting with a user via the wireless system, in accordance with some embodiments described herein.

FIG. 15 is a flow diagram of an example process 1500 for a medical practitioner (e.g., medical doctor). In some embodiments, the process 1500 begins with step 1502, in which a referring medical practitioner opens the app 104. Next, in step 1504, the medical practitioner enters a patient's information, data, and the desired control protocol for the system. In step 1606, the app 104 on the referring device 106 sends an invitation to the patient's user device 102, which then sends follow-up setup instructions to the patient in step 1508. The patient/user then creates an account in the app 104 in step 1510. The application, in step 1512, requests account verification and, in step 1514, the patient/user verifies the account. In step 1516, the app 104 requests data sharing privileges with the referring medical practitioner. In step 1518, the patient/user authorizes data sharing with the referring medical practitioner, and the app 104 notifies the referring medical practitioner of his or her data sharing authorization in step 1520. In step 1522, the medical practitioner receives a notification from the app 104 that the data sharing and set-up were successful.

Figure 16:
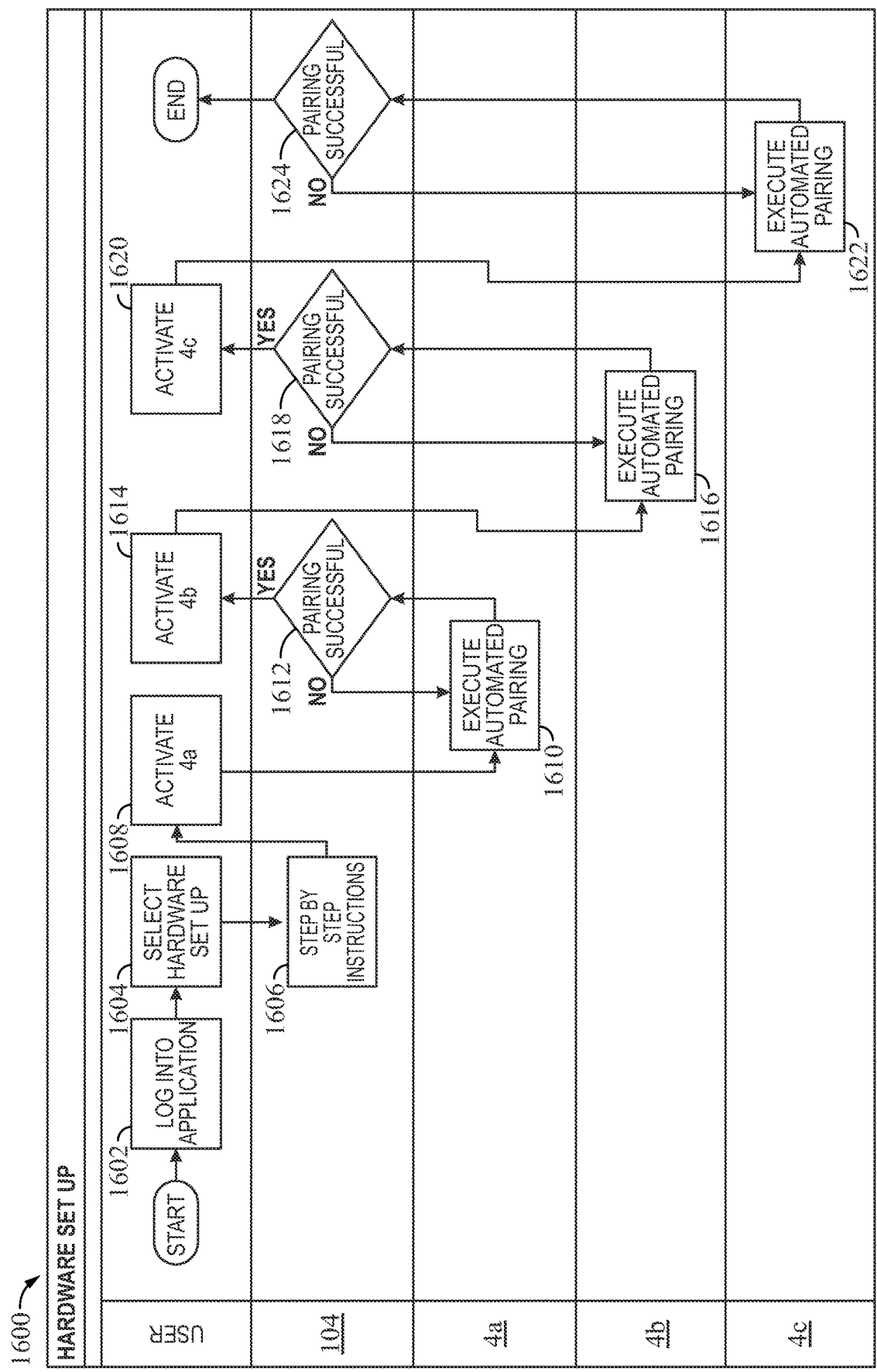
FIG. 16 is a flow diagram illustrating a process of a user activating a PPC and establishing communication between the PPC and the user device, in accordance with some embodiments described herein.

FIG. 16 is a flow diagram of an example process 1600 for setting up the hardware unit (10) in one or more PPCs (4a, 4b, 4c, etc.) using the app 104 on the patient's user device 102. In some embodiments, the process 1600 begins with step 1602, in which the user opens and logs into the app 104. Next, in step 1604, the user selects the Hardware Setup Function, and in step 1606, the app 104 provides the user with step-by-step instructions for the setup process. In step 1608, the user activates a first PPC 4a, and in step 1610, the first PPC 4a executes an automated pairing with the app 104. If the pairing is successful, then the process proceeds to step 1612. If the pairing is not successful, then the process repeats step 1610. In step 1412, the user selects a second PPC 4b in the app 104, and in step 1614, the second PPC 4b executes an automated pairing with the app 104. If the pairing is successful, then the process proceeds to step 1616. If the pairing is not successful, then the process repeats step 1614. In step 1414, the user selects a third PPC 4c in the app 104, and in step 1616, the third PPC 4c executes an automated pairing with the app 104. If the pairing is successful, then the process proceeds is complete. But if the pairing is not successful, then the process repeats step 1616. After each of the one or more PPCs has been activated and paired with the app 104, the hardware set up process is complete.

Figure 17:
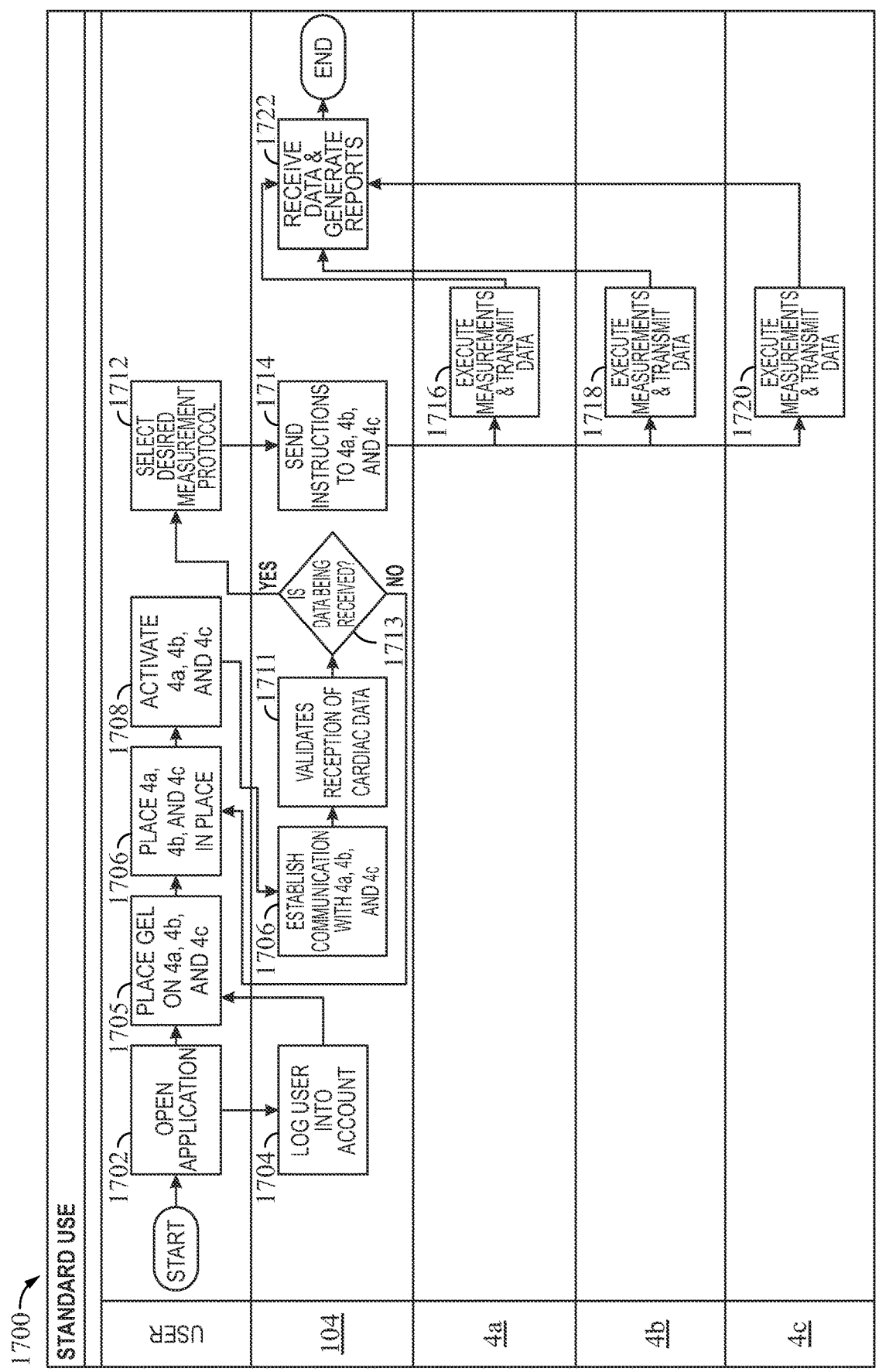
FIG. 17 is a flow diagram illustrating a process of the user operating the system, in accordance with some embodiments described herein.

FIG. 17 is a flow diagram of an example process 1700 for daily use of the system. In some embodiments, the process 1700 begins with step 1702, in which the user opens and logs into the app 104. In step 1704, the app 104 receives the user login information and logs the user into his or her account. In step 1706, the user then attaches the systems contained on a first wearable substrate 60a, a second wearable substrate 60b, and a third wearable substrate 60c to various areas of the user's body. In step 1708, the user activates the PPCs (4a, 4b, 4c) associated with each wearable substrate (60a, 60b, 60c). In step 1710, the app 104 establishes communication with each of the PPCs (4a, 4b, 4c) and each PPC establishes communication with the other PPCs (e.g., 4a establishes communication with 4b and 4c). In step 1712, the user selects the desired measurement protocol from a selection menu provided by the app 104. In step 1714, the app 104 sends instructions to each of the PPCs (4a, 4b, 4c). In step 1716, each of the PPCs (4a, 4b, 4c) executes the measurement instructions (e.g., measure the cardiovascular indicators of heart function, comprising aortic pulse wave, pulse transit time, aortic pulse wave velocity, blood flow velocity, blood turbulence, or a combination thereof) and then transmits a data set based on the measurements to the app 104. In step 1718, the data transmitted by the PPCs is received by the app 104 and a report summarizing the data from the combined data sets is generated.

Figure 18:
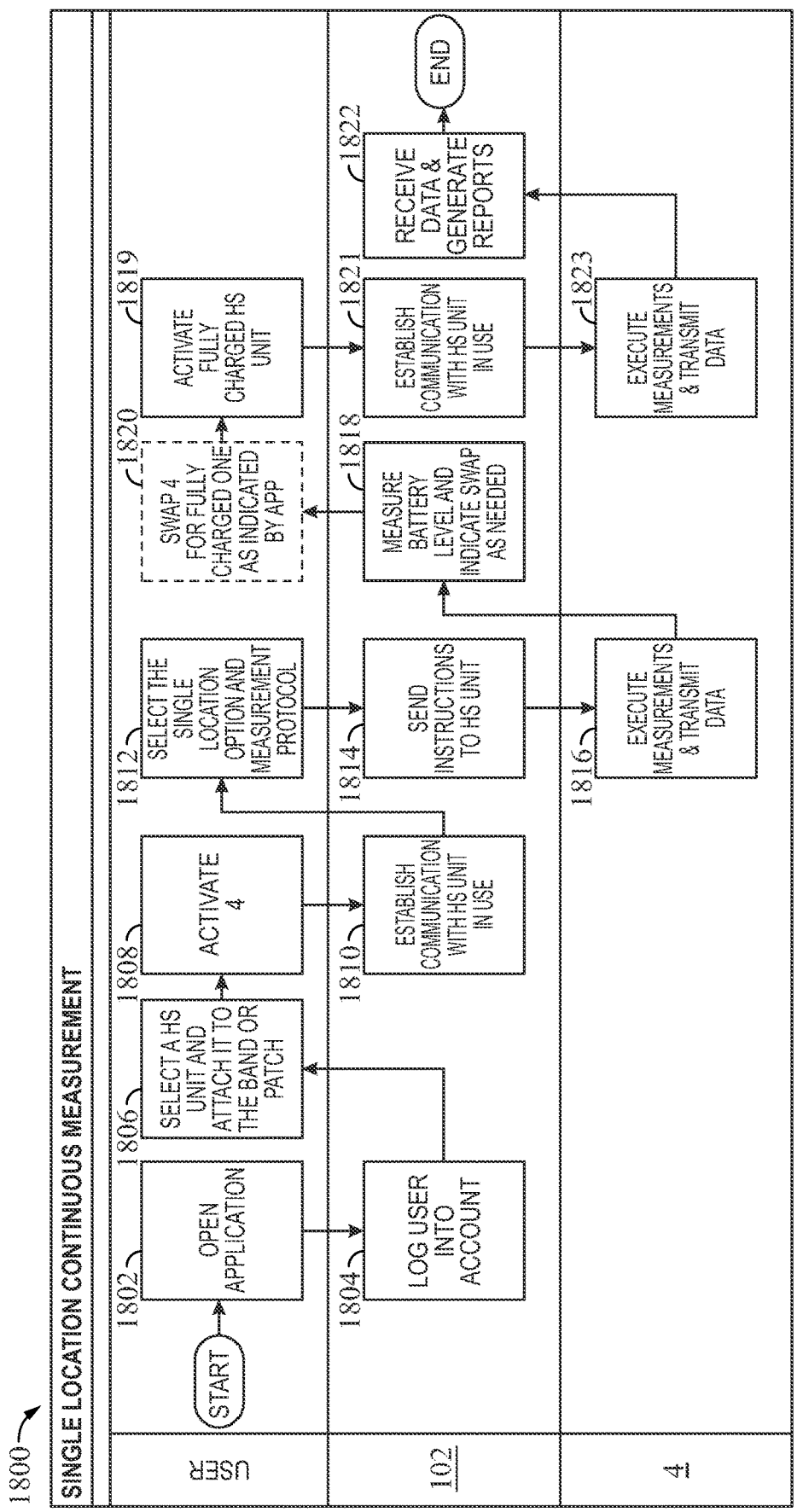
FIG. 18 is a flow diagram illustrating an alternative process of the user operating the system, in accordance with some embodiments described herein.

FIG. 18 is a flow diagram of an example process 1800 for a continuous measurement function for a PPC 4 positioned in a single location on the user. In steps 1802 and 1804, the user opens the app 104, and logs into his or her account. In step 1806, the user selects a PPC 4 to use and attaches it to a substrate (e.g., the flexible band embodiment 60 in FIG. 6), and activates the PPC 4 in step 1808. Next, the app 104 establishes communication with the selected and attached PPC 4 in step 1810. The user then selects the single location option, as well as the measurement protocol on the app 104 in step 1812. Next, in step 1814, the app 104 sends instructions to the PPC 4, which then executes measurements and transmits a data set to the app 104 in step 1816. In step 1818, the app 104 measures the battery level of the PPC 4 and indicates to the user as needed that the battery level is low and the PPC 4 should be replaced. Optionally, in step 1820, the user can then replace the PPC 4 in use for a PPC having additional battery life. In such embodiments, the next steps 1819 and 1821 include activating the charged puck 4 and executing measurements and data, respectively. In step 1822, the app 104 receives the data set transmitted from the PPC(s) and generates a report based on the data.

Figure 19:
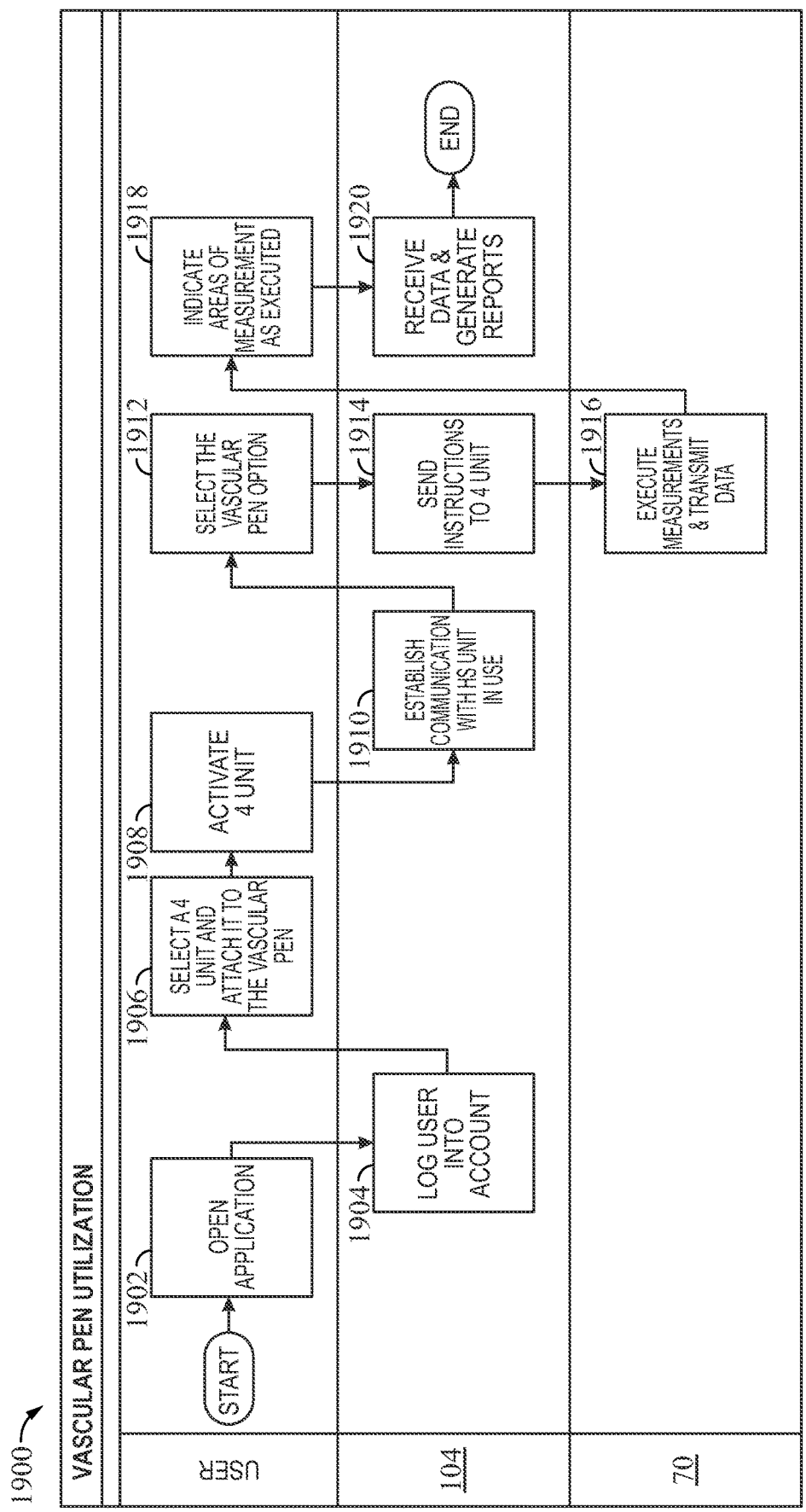
FIG. 19 is a flow diagram illustrating a process of a user operating the handheld wireless vascular pen in FIG. 7, in accordance with some embodiments described herein.

FIG. 19 is a flow diagram of an example process 1900 for operating an embodiment of the wireless system with a handheld substrate 70. In some embodiments, the process 1900 begins with step 1902, in which the user opens the app 104 on his or her user device 102. The next step 1904 requires the user to log into his or her account. Next, in step 1906, the user selects a PPC 4 and attaches it to the housing 72, as shown in FIG. 7. Once assembled, the user activates the PPC 4 in step 1908, and then, in step 1910, the user establishes communication between the activated PPC 4 and the app 104. In step 1912, the user selects the handheld embodiment 70 from a selection menu provided by the app 104. In step 1914, the app 104 sends instructions to the activated PPC 4 attached to the 70. In step 1916, the embodiment executes the measurement instructions (e.g., measure the cardiovascular indicators of heart function, comprising aortic pulse wave, pulse transit time, aortic pulse wave velocity, blood flow velocity, blood turbulence, or a combination thereof) and then transmits a data set based on the measurements to the app 104. In step 1918, the user then indicates in the app 104 which measurements (cardiovascular indicators of heart function) were executed. Next, in step 1920, the data transmitted by the PPC 4 on the pen 70 is received by the app 104 and a report summarizing the data set is generated.

Figure 20:
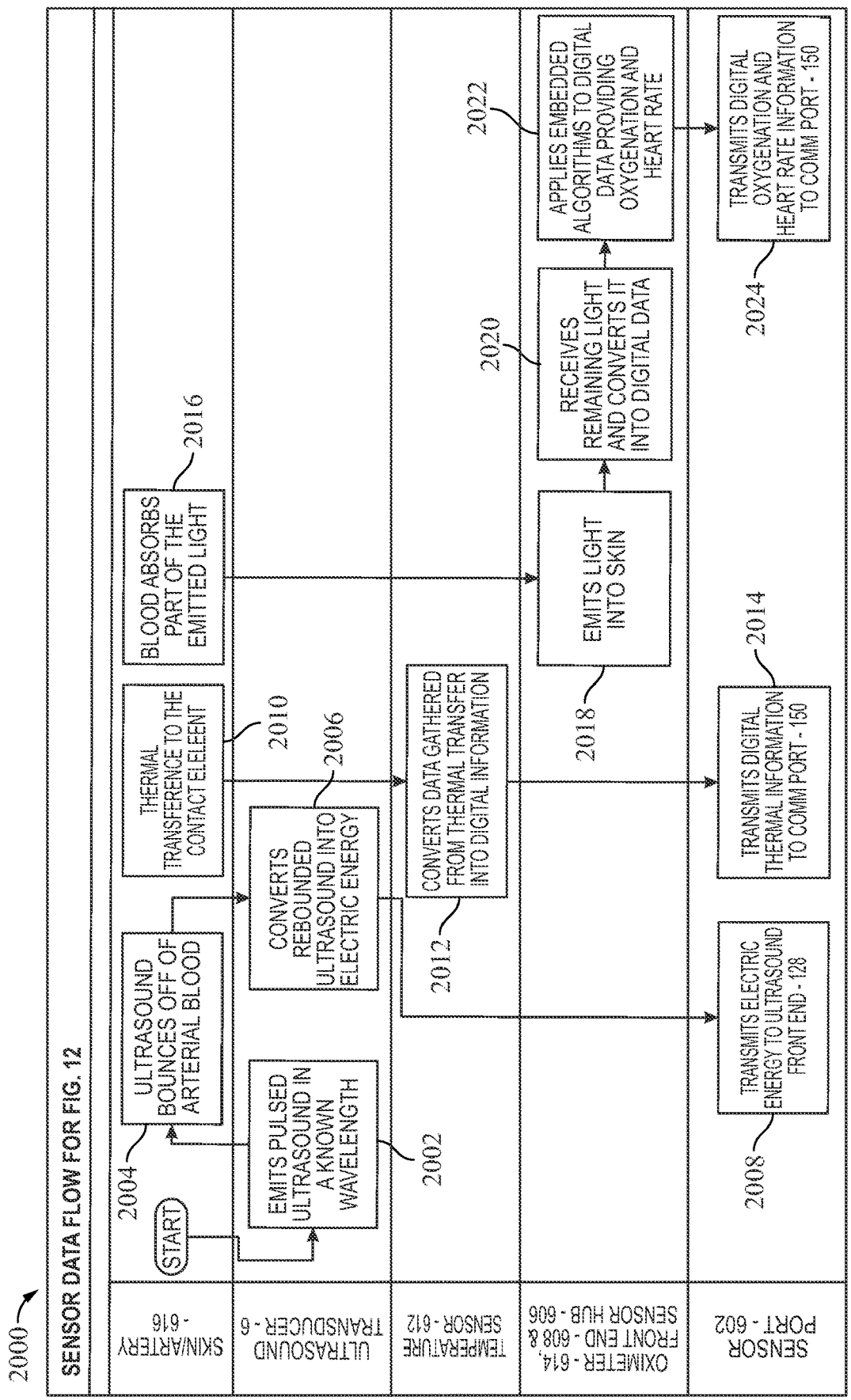
FIG. 20 is a flow diagram illustrating a process for the sensor data of FIG. 12.

FIG. 20 is a flow diagram for an example process 2000, which relates to the sensor data flow for FIG. 12. In some embodiments, in step 2002, the probe 6 emits a pulsed ultrasound having a known wavelength towards a target in the user's blood (e.g., artery). In step 2004, the ultrasound wave bounces off of the arterial blood, and when the rebounded ultrasound is received by the probe 6, it is converted into electric energy in step 2006. Next, the electric energy is transmitted to the sensor port 602 in step 2008, which transmits the energy to the ultrasound front end 128. In some embodiments, in step 2010, thermal data is received from the user's skin and transferred to the temperature sensor 612. In step 2012, the thermal data is converted into digital information and sent to the sensor port 602. In step 2014, the digital information is transmitted to comm port 150. In some embodiments, in step 2016, the blood in a user's body absorbs part of any emitted light from the probe 6. In step 2018, the light is emitted into the skin is detected by an oximeter 614, and the front end 608 receives remaining light in step 2020 and converts it into digital data. In step 2022, the sensor hub 606 applies embedded algorithms to the digital data to provide oxygenation and heart rate information, which is transmitted in step 2024 to the comm port 150 and sensor port 602.

Figure 21:
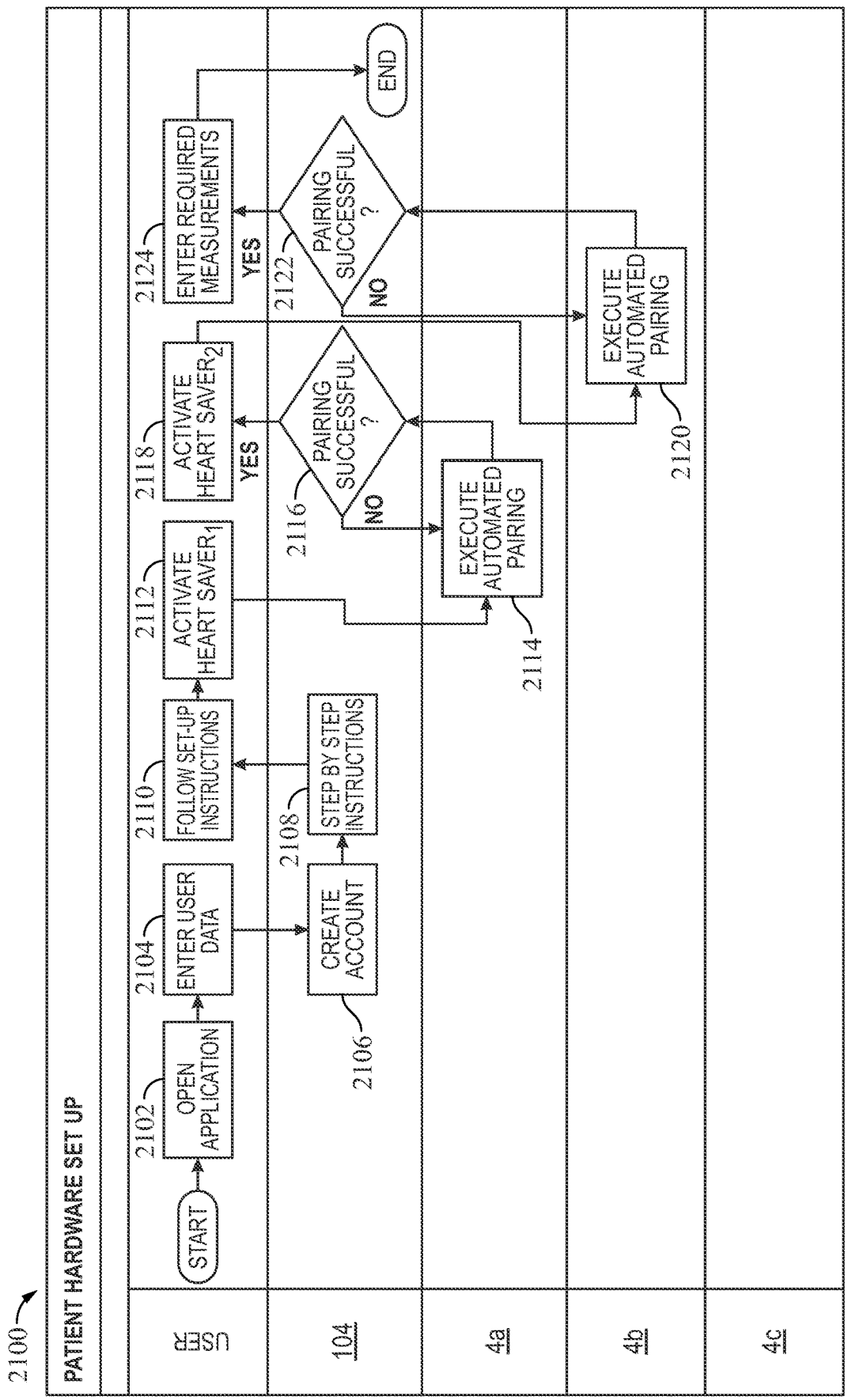
FIG. 21 is a flow diagram illustrating a process for the setup of a user's hardware, in accordance with some embodiments described herein.

FIG. 21 is a flow diagram for example process 2100, which relates to when a user is setting up the hardware of the system. In some embodiments, the user beings by opening the application in step 2002, entering user data in step 2004, and creating an account in the app 104 in step 2106. In step 2108, the app 104 provides instructions to the user, and in step 2110 the user follows the set-up instructions. In step 2112, the user activates a PPC 4a, which executes automated pairing with the app 104 in step 2114. In step 2116, if the pairing is successful, then the user activates a second PPC 4b in step 2118. If the pairing is not successful, then step 2114 is repeated. After the user activates a second PPC 4b in step 2118, the PPC 4b executes an automated pairing with the app 104 in step 2120. In step 2112, if the pairing is successful, then the user enters the required measurements in step 2124. If the pairing is not successful, then step 2120 is repeated.

In various embodiments the system 100 provides a synchronous comparison of the data gathered by the plurality of combination devices 2 (PPC 4 and probe 6). When the devices are activated and synchronized with one another, the system allows for the measurement of minute differences in the aortic pulse wave, transit time, blood flow, blood velocity, blood turbulence, etc. The plurality of combination devices 2 are not repetitive but work collectively in the system 100. This capability allows for an algorithmic comparison of the data sets and therefore an evaluation of the multiple cardiac indicators and associated conditions.

The foregoing is provided for purposes of illustrating, explaining, and describing embodiments of this disclosure. Modifications and adaptations to these embodiments will be apparent to those skilled in the art and may be made without departing from the scope or spirit of this disclosure.

Although the subject matter has been described in terms of exemplary embodiments, it is not limited thereto. Rather, the appended claims should be construed broadly, to include other variants and embodiments, which may be made by those skilled in the art.

What is claimed is:

1. A wireless system for measuring and analyzing blood in a body of a user, the wireless system comprising:
a plurality of devices operatively connected and synchronized with one another, each one of the plurality of devices configured to simultaneously ascertain, at different parts of the body of the user, the same biometric data associated with the blood in the body of the user, each one of the plurality of devices comprising:
a processing, power, and communication (PPC) component comprising a hardware unit and a first housing enclosing the hardware unit;
a probe comprising a piezoelectric crystal and a second housing enclosing the piezoelectric crystal, wherein the second housing is a spaced distance apart from the first housing;
a dock comprising a sensor and a third housing enclosing the sensor, wherein the third housing is adapted to removably coupled to the first housing,
the probe further comprising an acoustic barrier positioned between the second housing and the piezoelectric crystal,
the piezoelectric crystal being positioned between a first acoustic matching layer and a second acoustic matching layer, the acoustic barrier being configured and dimensioned to enclose the piezoelectric crystal, the first acoustic matching layer and the second acoustic matching layer, the first acoustic matching layer configured to cover a front face of the piezoelectric crystal and the second acoustic matching layer being configured to cover a rear face of the piezoelectric crystal, the piezoelectric crystal being configured to transmit an ultrasound wave into the body of the user, receive a return ultrasonic wave, convert the return ultrasonic wave into an electronic signal, and transmit the electronic signal to the sensor, the sensor being configured to receive the electronic signal from the piezoelectric crystal and transmit the electronic signal to the hardware unit, which is configured to wirelessly transmit a data set based on the electronic signal to a computer device, and the plurality of devices collectively configured to provide a synchronous comparison of the ascertained biometric data associated with the blood in the body of the user.

2. A wireless system for measuring and analyzing blood in a body of a user, the wireless system comprising:

a plurality of devices operatively connected and synchronized with one another, each one of the plurality of devices configured to simultaneously ascertain, at different parts of the body of the user, the same biometric data associated with the blood in the body of the user; each one of the plurality of devices comprising:

a processing, power, and communication (PPC) component comprising a hardware unit and a first housing enclosing the hardware unit;

a probe comprising a piezoelectric crystal and a second housing enclosing the piezoelectric crystal, wherein the second housing is a spaced distance apart from the first housing; and a dock comprising a sensor and a third housing enclosing the sensor, wherein the third housing is adapted to removably coupled to the first housing, the sensor comprising at least one of: a heart rate monitor configured to monitor a heart rate of the user, an oximeter configured to ascertain an oxygen level of the blood in the body of the user, or a temperature sensor configured to ascertain a temperature associated with the blood in the body of the user, the piezoelectric crystal being configured to transmit an ultrasound wave into the body of the user, receive a return ultrasonic wave, convert the return ultrasonic wave into an electronic signal, and transmit the electronic signal to the sensor;

the sensor being configured to receive the electronic signal from the piezoelectric crystal and transmit the electronic signal to the hardware unit, which is configured to wirelessly transmit a data set based on the electronic signal to a computer device, and the plurality of devices collectively configured to provide a synchronous comparison of the ascertained data associated with the blood in the body of the user.

3. The wireless system of claim 2, wherein the hardware unit of each one of the plurality of devices is disposed in wireless communication with a user device.

4. The wireless system of claim 3, wherein the user device comprises an analytical software configured to interpret and synchronize each data set received from the plurality of devices.

5. The wireless system of claim 3, wherein the user device is configured to display information based on the synchronized data sets.

6. The wireless system of claim 5, wherein the information comprises cardiovascular indicators of heart function, comprising:

aortic pulse wave;
pulse transit time;
aortic pulse wave velocity; blood flow velocity;
blood turbulence; or
a combination thereof.

* * * * *